US007476513B2

(12) United States Patent
Murphy et al.

(10) Patent No.: US 7,476,513 B2
(45) Date of Patent: *Jan. 13, 2009

(54) MONOCLONAL ANTIBODY SPECIFIC FOR THE EXTRACELLULAR DOMAIN OF PROSTATE SPECIFIC MEMBRANE ANTIGEN

(75) Inventors: Gerald P. Murphy, Seattle, WA (US); Alton L. Boynton, Bethesda, MD (US); Eric H. Holmes, Bothell, WA (US); William T. Tino, Redmond, WA (US)

(73) Assignee: Medarex, Inc., Princeton, NJ (US)

( * ) Notice: Subject to any disclaimer, the term of this patent is extended or adjusted under 35 U.S.C. 154(b) by 407 days.

This patent is subject to a terminal disclaimer.

(21) Appl. No.: 11/150,507

(22) Filed: Jun. 9, 2005

(65) Prior Publication Data

US 2007/0128671 A1 Jun. 7, 2007

Related U.S. Application Data

(60) Continuation of application No. 09/561,462, filed on Apr. 28, 2000, now Pat. No. 7,381,407, which is a division of application No. 09/044,668, filed on Mar. 18, 1998, now Pat. No. 6,150,508.

(51) Int. Cl.
*G01N 33/574* (2006.01)
*A61K 38/00* (2006.01)

(52) U.S. Cl. .......................... 435/7.23; 435/7.1; 424/9.1

(58) Field of Classification Search .................. None
See application file for complete search history.

(56) References Cited

U.S. PATENT DOCUMENTS

| | | | |
|---|---|---|---|
| 5,036,003 A | 7/1991 | Olander et al. | |
| 5,153,118 A | 10/1992 | Wright, Jr. et al. | |
| 5,162,504 A | 11/1992 | Horoszewicz | |
| 5,227,471 A | 7/1993 | Wright, Jr. | |
| 5,453,359 A | 9/1995 | Gargan et al. | |
| 5,489,525 A | 2/1996 | Pastan | |
| 5,538,866 A | 7/1996 | Israeli et al. | |
| 5,643,786 A | 7/1997 | Cohen et al. | |
| 5,773,292 A | 6/1998 | Bander | |
| 5,855,866 A | 1/1999 | Thorpe et al. | |
| 6,051,230 A | 4/2000 | Thorpe et al. | |
| 6,107,090 A | 8/2000 | Bander | |
| 6,136,311 A | 10/2000 | Bander | |
| 6,150,508 A | 11/2000 | Murphy et al. | |
| 6,194,152 B1 | 2/2001 | Laus et al. | |
| 6,953,668 B1 * | 10/2005 | Israeli et al. | 435/7.23 |
| 2004/0033229 A1 | 2/2004 | Maddon et al. | |
| 2004/0180002 A1 * | 9/2004 | Young et al. | 424/1.49 |

FOREIGN PATENT DOCUMENTS

| | | |
|---|---|---|
| CA | 2250141 | 10/1997 |
| EP | 02/28243 | 7/1987 |
| WO | WO-94/02156 | 2/1994 |
| WO | WO 94/09820 | 5/1994 |
| WO | WO-94/09820 | 5/1994 |
| WO | WO-96/08570 | 3/1996 |
| WO | WO-96/26272 | 8/1996 |
| WO | WO-96/39185 | 12/1996 |
| WO | WO-97/35616 A1 | 10/1997 |
| WO | WO-98/03873 | 1/1998 |
| WO | WO-99/47554 A1 | 9/1999 |
| WO | WO-01/09192 A1 | 2/2001 |
| WO | WO-02/069907 | 9/2002 |
| WO | WO-03/034903 A2 | 5/2003 |
| WO | WO-03/064606 | 8/2003 |

OTHER PUBLICATIONS

Bowie et al (Science, 1990, 257:1306-1310).*
Burgess et al ( J of Cell Bio. 111:2129-2138, 1990).*
Lazar et al (Molecular and Cellular Biology, 1988, 8:1247-1252).*
Christiansen et al (Mol Cancer Ther, 2004, 3:1493-1501).*
Topp et al (Journal of Controlled Release, 1998, 53:15-23).*
Gura (Science, 1997, 278:1041-1042).*
Kaiser (Science, 2006, 313, 1370).*
Chien, Nadine C. et al, "Significant structural and functional change of an antigen-binding site by a distant amino acid substitution: Proposal of a structural mechanism," *Proc. Natl. Acad. Sci. USA*, vol. 86:5532-5536 (1989).
Giusti, Angela M. et al, "Somatic diversification of S107 from an antiphosphocholine to an anti-DNA autoantibody is due to a single base change in its heavy chain variable region," *Proc. Natl. Acad. Sci. USA*, vol. 84:2926-2930 (1987).
Güssow, Detlef et al, "Humanization of Monoclonal Antibodies," *Methods in Enzymology*, vol. 203:99-121 (1991).
Jakobovits, Aya, "The long-awaited magic bullets: therapeutic human monoclonal antibodies from transgenic mice," *Expert Opinion on Investigational Drugs*, vol. 7(4):607-614 (1998).
Mariuzza, R.A., "The Structural Basis of Antigen-Antibody Recognition," *Ann. Rev. Biophys. Biophys. Chem.*, vol. 16:139-159 (1987).
Pohl, C. et al, "CD30-Specific AB1-AB2-AB3 Internal Image Antibody Network: Potential Use As Anti-Idiotype Vaccine Against Hodgkin's Lymphoma," *Int. J. Cancer*, vol. 54:418-425 (1993).
International Search Report for Application No. PCT/US97/05214, dated Jul. 9, 1997.
Beutler et al., "L-Glutamate, Colorimetric Method with Glutamate Dehydrogenase and Diaphorase, Methods of Enzymaytic Analysis," Bergmeyer et al. Eds, 1985 VCH Publishers, Deerfield Beach, pp. 369-376.
Bruggeman, M., et al., "Dtrategies for expressing human antibody repertoires in transgenic mice," *Immunol. Today*, 17(8):391-97 (aug. 17, 1996).
Carter et al., "Prostate-specific Membrane Antigen is a Hydrolase with Substrate and Pharmacologic Characteristics of a Neuropeptidase," *Proc. Natl., Acad. Sci. U.S.A.* 93:749-751 (1996).

(Continued)

*Primary Examiner*—Sheela J Huff
(74) *Attorney, Agent, or Firm*—Lahive & Cockfield, LLP; Jane E. Remillard, Esq.

(57) ABSTRACT

The present invention relates to monoclonal antibodies that bind to the extracellular domain of prostate-specific membrane antigen (PSMA), hybridoma cell lines producing the antibodies, and methods of using such antibodies for diagnosis and treatment of cancer. In particular, thirty-five monoclonal antibodies reactive with PSMA expressed on the cell surface are exemplified. Additionally, the present invention relates to a novel protein variant (PSM') of PSMA detected by a number of the antibodies of the invention. The hydrolase activity of PSMA and PSM' allows the use of an immunoenzymatic assay for their detection.

16 Claims, 20 Drawing Sheets

OTHER PUBLICATIONS

Figure 2:
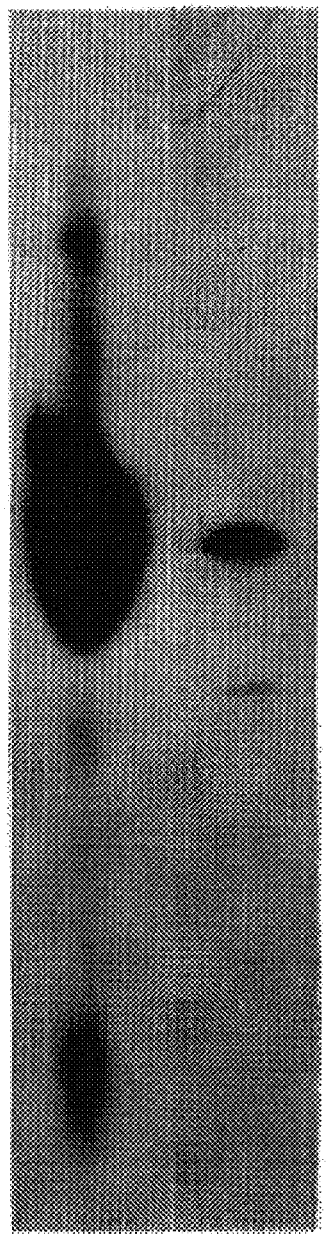

Chang et al., "Five different Anti-Prostate-specific Membrane Antigen (PSMA) Antibodies Confirm PSMA Expression in Tumor-associated Neovasculature," *Cancer Research*, Jul. 1, 1999, 59:3192-3198.

Chang et al., "Prostate-specific Membrane Antigen Is Produced in Tumor-associated Neovasculature," *Clinical Cancer Research*, Oct. 1999, 5:2674-2681.

Curnow, RT. "Clinical experience wit CD64-directed immunotherapy. An overview." *Cancer Immunol. Immunoither.*, 45(3-4):210-15 (Nov.-Dec. 1997).

Fernandez et al., "Influence of Epitope Polarity and Adjuvants on the Immunogenicity and Efficacy of a Synthetic Peptide Vaccine Against Semliki Forest Virus," *Journal of Virology* 67:5843-8 (1993).

Fernandez, et al., "Epitope Polarity and Adjuvants Influence the Fine Specificity of the Humoral Response Against Emliki Forest Virus Specific Peptide Vaccines," *Vaccine* 16:1531-6 (1998).

Gong, M.C., et al., "Prostate-specific membrane antigen (PSMA)-specific monoclonal antibodies in the treatment of prostate and other cancers," *Cancer Metastasis Rev.*, 18(4):483-90 (1999).

Green, L.L., "Antibody engineering via genetic engineering of the mouse: XenoMouse strains are a vehicle for the facile generation of therapeutic human monoclonal antibodies," *J. Immunol. Methods*, 231(1-2): 11-23 (Dec. 10, 1999).

Hamilton, A. et al., "A novel humanised antibody against Prostate Specific Membrane Antigen (PSMA) for in vivo targeting and therapy." Proceedings of the American Association for Cancer Research Annual Meeting: 89th Annual Meeting of the American Association for Cancer Research; New Orleans, Louisiana, USA. vol. 39 (Mar. 1998).

He Liu et al., 1997, "Monoclonal Antibodies to the Extracellular Domain of Prostate-Specific Membrane Antigen Also React with Tumor Vascular Endothelium", *Cancer Res.* 57:3629-3634.

Holmes Eh et al., "Development and Characterization of Monoclonal Antibodies Specific for the Extracellular Domain of Prostate-Specific Membrane Antigen", *Cancer Biotherapy and Radiopharmaceuticals*, vol. 13, No. 1, Feb. 1998, p. 12, XP009046764.

Holmes, "PSMA Specific Antibodies and Their Diagnostic and Therapeutic Use," *Exp. Opin. Invest. Drugs* 10 3:511-519 (2001).

Holmes, et al., "Analysis of glycosylation of prostate-specific membrane antigen drived from LNCaP cells, prostatic carcinoma tumors, and serum from prostate cancer patients," *Prostate* 1996 United States, vol. 29, No. Suppl. 7, 1996, pp. 25-29, XP000983731.

Horoszewicz et al., "Monoclonal Antibodies to a New Antigenic Marker in Epithelial Prostatic Cells and Serum of Prostatic Cancer Patients," *Anticancer Research* 7:927-936 (1987).

Israeli et al., "Expression of the Prostate-specific Membrane Antigen," *Cancer Res.* 54:1807-1811 (1994).

Israeli et al., "Molecular Cloning of a Complementary DNA Encoding a Prostate-specific Membrane Antigen," *Cancer Res.* 53:227-230 (1993).

Leek et al., "Prostate-Specific Membrane Antigen: Evidence fro the Existence of a Second Related Human Gene," *British Journal of Cancer* 72:583-588 (1995).

Murphy et al., "Comparison of Prostate Specific Membrane Antigen, and Prostate Specific Antigen Leels in Prostatic Cancer Patients," *Anticancer Res.* 15:1473-1480 (1995).

Murphy et al., "Comparison of Prostate Specific Antigen, Prostate Specific Membrane Antigen, and LNCaP-Based Enzyme-Linked Immunosorbent Assays in Prostatic Cancer Patients and Patients With Benign Prostatic Enlargement," *the Prostate* 26:164-168 (1995).

Murphy et al., "Measurement of Prostate-Specific Membrane Antigen in the Serum With a New Antibody," *The Prostate* 28:266-271 (1996).

Murphy et al., "Measurement of serum prostate-specific membrane antigen, a new prognostic marker for prostate cancer," *Urology*, May 1998, vol. 51, No. 5A Suppl., May 1998, pp. 89-97, XP002312669.

Nakamura et al., "Enzyme immunoassays: heterogeneous and homogeneous systems," Handbook of Exp. Immunol., Weir et al., Eds. Blackwell Scientific Publications, Oxford, 1:2711-2720 (1987).

Prostate Cancer Patients, *The Prostate* 25:219-223.

Rochon et al., "Western Blot Assay for Prostate-Specific Membrane Antigen in Serum of Prostate Cancer Patients," *The Prostate* 25:219-223 (1994).

Roitt et al., Immunology, 3rd Ed., Mosby, St. Louis, p. 106 (1993).

Sharkey et al., "Enhanced Clearance of Radiolabeled Murine Monoclonal Antibody by a Syngeneic Anti-Idiotype Antibody in Tumor-bearing Nude Mice," *Int. J. Cancer* 51:266-273 (1992).

Su et al., "Alternatively Spliced Variants of Prostate-specific Membrane antigen RNA: Ratio of Expression as a Potential Measurement of Progression," *Cancer Res.* 55:1441-1443 (1995).

Tjoa et al., "In Vitro Propagated Dendritic Cells from Prostate Cancer Patients as a Component of Prostate Cancer Immunotherapy," *The Prostate*, 27:63-69 (1995).

Troyer et al., "Biochemical Characterization and Mapping of the 7E11-C5.3 Epitope of the Prostate-Specific Membrane Antigen," *Urol. Oncol.* 1:29-37 (1995).

Troyer et al., "Detection and characterization of the Prostate-Specific Membrane Antigen (PSMA) in Tissue Extracts and Body Fluids," *Int. J. Cancer* 62:552-558 (1995).

Troyer et al., "Subcellular Localization of the 7E11-C5 Prostate Specific Antigen," *Proc. Am. Assoc. Cancer Res.* 35:283 Abstract 1688 (1994).

Vaughn, TJ, et al., "Human antibodies by design." *Natl. Biotechnol.*, 16(6):535-9 (Jun. 1998).

Wright, "Characterization of a New Prostate Carcinoma-Associated Marker: 7E11-C5," *Antibody Immunoconjugates and RadioPharmaceuticals* 3:Abstract 193 (1990).

Murphy, G.P. et al.: "Measurement of serum prostate-specific membrane antigen, a new prognostic marker for prostate cancer." Urology, May 1998, vol. 51, No. 5A Suppl., May 1998, pp. 89-97, XP002312669.

Holmes, E.H. et al.: "Analysis of glycosylation of prostate-specific membrane antigen derived from LNCaP cells, prostatic carcinoma tumors, and serum from prostate cancer patients," Prostate 1996 United States, vol. 29, No. Suppl. 7, 1996, pp. 25-29, XP000983731.

Bander, Neil H. et al., "Phase I Trial of $^{177}$Lutetium-Labeled J591, a Monoclonal Antibody to Prostate-Specific Membrane Antigen, in Patients With Androgen-Independent Prostate Cancer," *J. Clin. Oncol.*, vol. 23:4591-4601 (2005).

Caldas, Cristina et al., "Humanization of the anti-CD18 antibody 6.7: an unexpected effect of a framework residue in binding to antigen," *Molecular Immunology*, vol. 39:941-952 (2003).

Donovan, Gerald P. et al., "Antibody and Vaccine Therapies Targeting Prostate Specific Membrane Antigen (PSMA)," *Proceedings of the American Association for Cancer Research*, vol. 42:818 (2001).

Greenspan, Neil S. et al., "Defining epitopes: It's not easy as it seems," *Nature Biotechnology*, vol. 17:936-937 (1999).

Jiang, Beihai et al., "A Novel Peptide Isolated from a Phage Display Peptide Library with Trastuzumab Can Mimic Antigen Epitope of HER-2," *The Journal of Biological Chemistry*, vol. 280(6):4656-4662 (2005).

Morris, Michael J. et al., "Pilot Trial of Unlabeled and Indium-111-Labeled Anti-Prostate-Specific Membrane Antigen Antibody J591 for Castrate Metastatic Prostate Cancer," *Clin. Cancer. Res.*, vol. 11(20):7454-7461 (2005).

O'Keefe, Denise S. et al., "Comparative Analysis of Prostate-Specific Membrane Antigen (PSMA) Versus a Prostate-Specific Membrane Antigen-Like Gene," *The Prostate*, vol. 58:200-210 (2004).

Pohl, Christoph et al., "CD-30-Antigen-Specific Targeting and Activation of T Cells via Murine Bispecific Monoclonal Antibodies Against CD3 and CD28: Potential Use for the Treatment of Hodgkin's Disease," *Int. J. Cancer*, vol. 54:820-827 (1993).

Schmittgen, Thomas D. et al., "Expression of Prostate Specific Membrane Antigen and Three Alternatively Spliced Variants of PSMA in Prostate Cancer Patients," *Int. J. Cancer*, vol. 107:323-329 (2003).

Stancovski, Ilana et al., "Mechanistic aspects of the opposing effects of monoclonal antibodies to the ERBB2 receptor on tumor growth," *Proc. Natl. Acad. Sci. USA*, vol. 88:8691-8695 (1991).

US 6,290,956, 09/2001, Bander (withdrawn)

* cited by examiner

FIG. 1

| | |
|---|---:|
| MWNLLHETDSAVATARRPRWLCAGALVLAGGFFLLGFLFGWFIKSSNEATNITPKHN | 57 |
| MKAFLDELEKAENIKKFLYNFTQIPHLAGTEQNFQLAKQIQSQWKEFGLDSVELAHYDVL | 116 |
| LSYPNKTHPNYISIINEDGNEIFNTSLFEPPPPGYENVSDIVPPFSAFSPQGMPEGDL | 174 |
| VYVNYARTEDFFKLERDMKINCSGKIVIARYGKVFRGNKVKNAQLAGAKGVILYSDPA | 232 |
| DYFAPGVKSYPDGWNLPGGGVQRGNILNLNGAGDPLTPGYPANEYAYRRGIAEAVGLP | 290 |
| SIPVHPIGYYDAQKLLEKMGGSAPPDSSWRGSLKVPYNVGPGFTGNFSTQKVKMHIHS | 348 |
| TNEVTRIYNVIGTLRGAVEPDRYVILGGHRDSWVFGGIDPQSGAAVVHEIVRSFGTLK | 406 |
| KEGWRPRRTILFASWDAEEFGLLGSTEWAEENSRLLQERGVAYINADSSIEGNYTLRV | 464 |
| DCTPLMYSLVHNLTKELKSPDEGFEGKSLYESWTKKSPSPEFSGMPRISKLGSGNDFE | 522 |
| VFFQRLGIASGRARYTKNWETNKFSGYPLYHSVYETYELVEKFYDPMFKYHLTVAQVR | 580 |
| GGMVFELANSIVLPFDCRDYAVVLRKYADKIYSISMKHPQEMKTYSVSFDSLFSAVKN | 638 |
| FTEIASKFSERLQDFDKSNPIVLRMMNDQLMFLERAFIDPLGLPDRPFYRHVIYAPSS | 696 |
| HNKYAGESFPGIYDALFDI*ESKVDPSKA*WGEVKRQIYVAAFTVQAAAETLSEVA | 750 |

FIG. 3
1 2 3 4
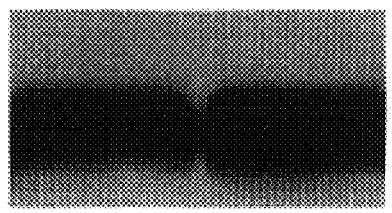 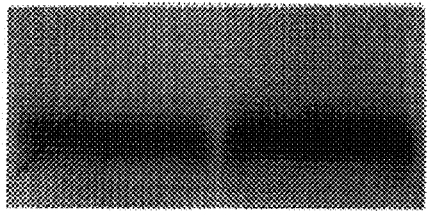

MONOCLONAL ANTIBODY SPECIFIC FOR THE EXTRACELLULAR DOMAIN OF PROSTATE SPECIFIC MEMBRANE ANTIGEN

This application is a continuation of U.S. application Ser. No. 09/561,462, filed Apr. 28, 2000, (now U.S. Pat. No. 7,381,407) which is a divisional of U.S. application Ser. No. 09/044,668, filed Mar. 18, 1998 (now U.S. Pat. No. 6,150,508) which is a continuation-in-part of application Ser. No. 08/827,017, filed Mar. 25, 1997 (abandoned), which is a continuation-in-part of application Ser. No. 08/621,399, filed Mar. 25, 1996 (abandoned). The contents of these applications are incorporated by reference in their entirety.

1. FIELD OF THE INVENTION

The present invention relates to monoclonal antibodies that bind to the extracellular domain of prostate-specific membrane antigen (PSMA), hybridoma cell lines producing the antibodies, and methods of using such antibodies for diagnosis and treatment of cancer. In particular, it relates to a monoclonal antibody generated against a synthetic peptide substantially homologous to a portion of the carboxyl terminal region of PSMA, which antibody reacts with PSMA expressed on tumor cell surface and in sera of prostate cancer patients. Additionally, it relates to thirty-four monoclonal antibodies generated against a prostatic carcinoma membrane preparation, which antibodies also react with PSMA expressed on the cell surface. The present invention also relates to a novel protein variant (PSM') of PSMA detected by the antibodies.

2. BACKGROUND OF THE INVENTION

Prostate cancer is the second leading cause of death from cancer among men. In fact, prostate cancer is the most common non-cutaneous cancer diagnosed in the American male. The number of men diagnosed with prostate cancer is steadily increasing as a result of the increasing population of older men as well as a greater awareness of the disease leading to its earlier diagnosis (Parker et al., 1997, CA Cancer J. for Clin. 47:5-28). It was projected that over 334,500 men would be diagnosed with prostate cancer in 1997, and that approximately 41,800 deaths would result from the disease. The life time risk for men developing prostate cancer is about 1 in 5 for Caucasians, and 1 in 6 for African Americans. High risk groups are represented by those with a positive family history of prostate cancer or African Americans. Over a lifetime, more than ⅔ of the men diagnosed with prostate cancer die of the disease (Wingo et al., 1996, CA Cancer J. for Clin. 46:113-25). Moreover, many patients who do not succumb to prostate cancer require continuous treatment to ameliorate symptoms such as pain, bleeding and urinary obstruction. Thus, prostate cancer also represents a major cause of suffering and increased health care expenditures (Catalona, 1994, New Eng. J. Med. 331:996-1004).

PSMA is a 120 kDa molecular weight protein expressed in prostate tissues and was originally identified by reactivity with a monoclonal antibody designated 7E11-C5 (Horoszewicz et al., 1987, Anticancer Res. 7:927-935; U.S. Pat. No. 5,162,504). PSMA was obtained in purified form (Wright et al., 1990, *Antibody Immunoconjugates and Radio Pharmaceuticals* 3:Abstract 193) and characterized as a type II transmembrane protein having sequence identity with the transferring receptor (Israeli et al. 1994, Cancer Res. 54:1807-1811) and with NAALADase activity (Carter et al., 1996, Proc. Natl. Acad. Sci. U.S.A. 93:749-753). More importantly, PSMA is expressed in increased amounts in prostate cancer, and elevated levels of PSMA are also detectable in the sera of these patients (Horoszewicz et al., 1987, supra; Rochon et al., 1994, Prostate 25:219-223; Murphy et al., 1995, Prostate 26:164-168; and Murphy et al., 1995, Anticancer Res. 15:1.473-1479). A cDNA encoding PSMA has been cloned (Israeli et al., 1993, Cancer Res. 53:227-230), and it produces two alternatively spliced mRNA species: an mRNA species containing 2,653 nucleotides that encodes PSMA, and a second mRNA species containing 2,387 nucleotides referred to as PSM' (Su et al., 1995, Cancer Res. 55:1441-1443). Prior to the present invention, it was not known whether PSM' encoded a protein product or existed only as an untranslated mRNA species because a PSM' protein product had never been detected. A recent report by Carter et al. (1996, Proc. Natl. Acad. Sci. U.S.A., 93:749-753) shows a high degree of identity between 1428 bases representing a portion of the PSMA cDNA and the cDNA sequence of protein N-acetylated α-linked acidic dipeptidase (NAALADase). NAALADase has enzymatic activity towards the neuropeptide N-acetylaspartyl glutamate to yield glutamate and N-acetylaspartate. This report demonstrates NAALADase activity inherent to PSMA protein, but the catalytic portion of PSMA was not identified. NAALADase activity was found in LNCaP cells which expressed PSMA, but not in PC3 cells which do not express PSMA. Transfection of the PSMA cDNA into PC3 cells produced NAALADase activity and the presence of PSMA in these cells.

The difference between the cDNA of PSMA and PSM' is the loss of the transmembrane and intracellular coding regions containing nucleotides #1-171 of SEQ ID NO:2 or amino acids #1-57 of SEQ ID NO: 2. PSMA is described as a type II membrane protein and it is known that the functional catalytic domain of type II membrane proteins resides in the C-terminal extracellular region of the molecule (DeVries, et al., 1995, J. Biol. Chem., 270:8712-8722).

PSM' mRNA is found in greater quantities in normal prostate tissues as compared with prostate tissues of patients with benign hyperplasia or prostate cancer (Su et al., 1995, supra). In contrast, PSMA mRNA is found in greater levels in patients with prostate cancer as compared to patients without prostate cancer (Su et al., 1995, supra). This observed difference is consistent with serum protein levels of PSMA described previously (Horoszewicz et al., 1987, supra; Rochon et al., 1994, supra; Murphy et al., 1995, supra; and Murphy et al., 1995, supra). In this connection, an elevated level of PSMA in sera of prostate cancer patients has been correlated with disease progression versus remission, and may be used as a prognostic marker (Murphy et al., 1995, supra).

The epitope recognized by monoclonal antibody 7E11-C5 has been mapped to the first 6 amino acids of the intracellular N-terminal region of PSMA (Troyer et al., 1995, Urol. Oncol. 1:29-37) (FIG. 1). Electron immunocytochemistry using 7E11-C5 has localized its epitope to the cytoplasm, and specifically to the inner leaf of the plasma membrane (Troyer et al., 1994, Proc. Am. Assoc. Cancer Res. 35:283, Abstract 1688). Furthermore, in in vitro tests, monoclonal antibody 7E11-C5 stains only fixed and permeabilized cells (Horoszewicz et al., 1987, supra), which is in accord with the mapping of the 7E11-C5 epitope to the N-terminus or intracellular domain of PSMA. While 7E11-C5 is useful for detecting prostate cancer in vivo which presumably exposes its epitope through necrosis and/or apoptosis, a monoclonal antibody specific for the extracellular domain of PSMA would allow more efficient detection of PSMA on the cancer cell surface. In addition, monoclonal antibody 7E11-C5 does not recognize PSM', since PSM' lacks the intracellular domain of PSMA, based on the sequence of its mRNA transcript.

Citation or identification of any reference in this section or in any other section of this application shall not be construed as an admission that such reference is available as prior art to the present invention.

3. SUMMARY OF THE INVENTION

The present invention relates to monoclonal antibodies specific for the extracellular domain of PSMA, hybridoma cell lines that produce the antibodies, and methods of using the antibodies for prostate cancer diagnosis, and treatment, as well as a variant protein form of PSMA known as PSM' recognized by such antibodies.

The invention is based, in part, on the Applicants' discovery of monoclonal antibodies that recognize the extracellular domain of PSMA. One antibody was generated by immunizing mice with a C-terminal peptide of PSMA having the amino acid sequence of ESKVDPSK (SEQ ID NO:1). The antibody reacts with PSMA and PSM' proteins in tumor cell lysates and in sera of prostate cancer patients. In addition, it stains intact live tumor cells, confirming its specificity for the extracellular domain of PSMA or PSM' protein. The antibody also detects PSM' in human seminal fluids, and the PSM' therein exhibits NAALADase activity. Additional exemplary monoclonal antibodies were also generated against a prostatic carcinoma membrane preparation. These antibodies react with the extracellular domain of PSMA, including native PSMA isolated by immunoaffinity purification and recombinant PSMA produced by recombinant DNA technology. Most of these antibodies also react with PSM' The antibodies of the invention are useful in combination with an antibody directed to the intracellular domain of PSMA in a two-site capture assay to detect the presence of PSMA in a test sample. Furthermore, the antibodies disclosed herein may be used in a two-site capture assay to detect the presence of PSM' in a test sample.

A wide variety of uses are encompassed by the present invention, including but not limited to, the development and use of an immunoassay to detect or stage prostate cancer in a patient, imaging of primary and/or metastatic prostate cancer in vivo, therapeutic uses of the antibodies, including uses of antibodies conjugated to a cytotoxic or chemotherapeutic agent; and the construction and use of antibody fragments, chimeric antibodies, humanized antibodies or bifunctional antibodies.

4. BRIEF DESCRIPTION OF THE DRAWINGS

FIG. 1. Deduced amino acid sequences of PSMA and PSM' antigens (SEQ ID NO:2) (Israeli et al., 1994 Cancer Res. 54:1807-1811). PSM' mRNA does not contain the 5' end of the PSMA that would encode the first 57 amino acids (first line of amino acid sequence) and thus presumably begins at amino acid 58. However, prior to the present invention, PSM' had never been identified in its protein form. Underlined region is the putative transmembrane domain and the bold region (amino acid #716-723 of SEQ ID NO:2) is a peptide selected for monoclonal antibody development.

FIG. 2. Demonstration of monoclonal antibody 3F5.4G6 (a subclone derived from primary hybridoma 3F5) and its reactivity with a protein present in LNCaP lysate of 120 kDa molecular weight corresponding to PSMA. Western blot was developed with HRP-anti-IgG secondary antibody. Lane 1=LNCaP lysate probed with 7E11-C5; Lane 2=LNCaP lysate probed with 3F5.4G6.

FIG. 3. Demonstration by western blot of PSMA in sera of prostate cancer patients (stage D2) using monoclonal antibodies 3F5.4G6 (Lanes 3 and 4) and 7E11-C5 (Lanes 1 and 2) as control.

Figure 4:
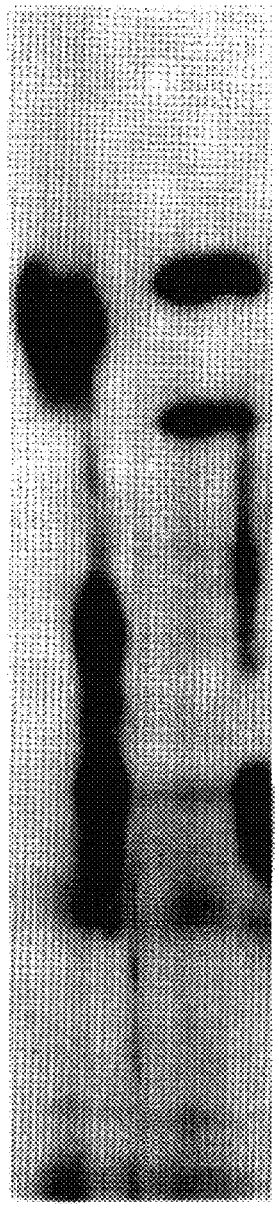

FIG. 4. Western blot assay of LNCaP lysates using monoclonal antibodies 7E11-C5 (Lane 1) and 3F5.4G6 (Lane 2) and developed with HRP-anti-IgM secondary antibody. Both 7E11-C5 and 3F5.4G6 recognized a protein of molecular weight 120 kDa. In addition, 3F5.4G6 also recognized a protein of 105-110 kDa molecular weight corresponding to the predicted protein form of PSM'. It should be noted that 7E11-C5 did not recognize PSM' because the epitope of 7E11-C5 monoclonal antibody was not found in PSM'. Antibody 3F5.4G6 recognizes the C-terminal portion of the protein (amino acid #716-723 of SEQ ID NO:2), which corresponds to the extracellular domain of PSMA and PSM'.

Figure 5:
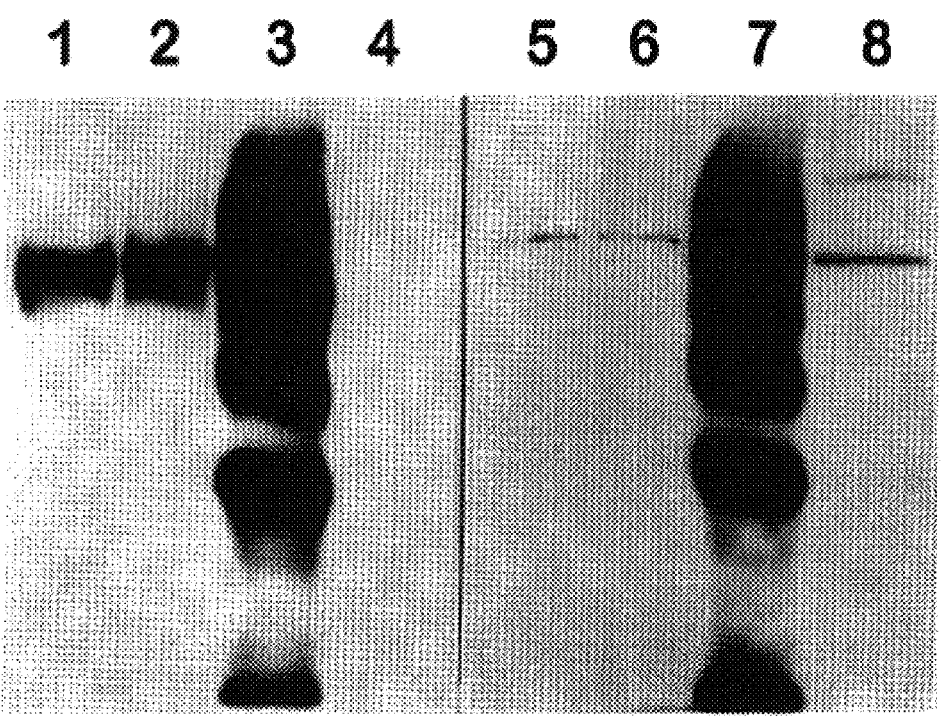

FIG. 5. Demonstration that monoclonal antibodies 7E11-C5 and 3F5.4G6 recognized an identical protein but that 3F5.4G6 recognized an additional protein corresponding to PSM'. LNCaP lysate was initially immunoprecipitated with 7E11-C5 monoclonal antibody and the immunoprecipitated material separated on SDS gels and probed in a Western blot assay with either 7E11-C5 (lanes 1-4) or with 3F5.4G6 (Lanes 5-8) monoclonal antibodies. Lanes 1 and 5 were crude LNCaP lysate; Lanes 2 and 6 were precleared LNCaP lysate; Lanes 3 and 7 were material which immunoprecipitated with 7E11-C5 monoclonal antibody; and Lanes 4 and 8 were proteins left in the previously immunoprecipitated LNCaP lysate. Antibody 7E11-C5 immunoprecipitated a protein of 120 kDa (Lane 3), which was also recognized by 3F5.4G6 (Lane 7). However, after 7E11-C5 immunoprecipitation, a second protein was recognized by 3F5.4G6 (Lane 8) that was not precipitated by 7E11-C5 (Lane 4), and which corresponded to PSM'. Thus, 7E11-C5 does not recognize PSM'.

Figure 6:
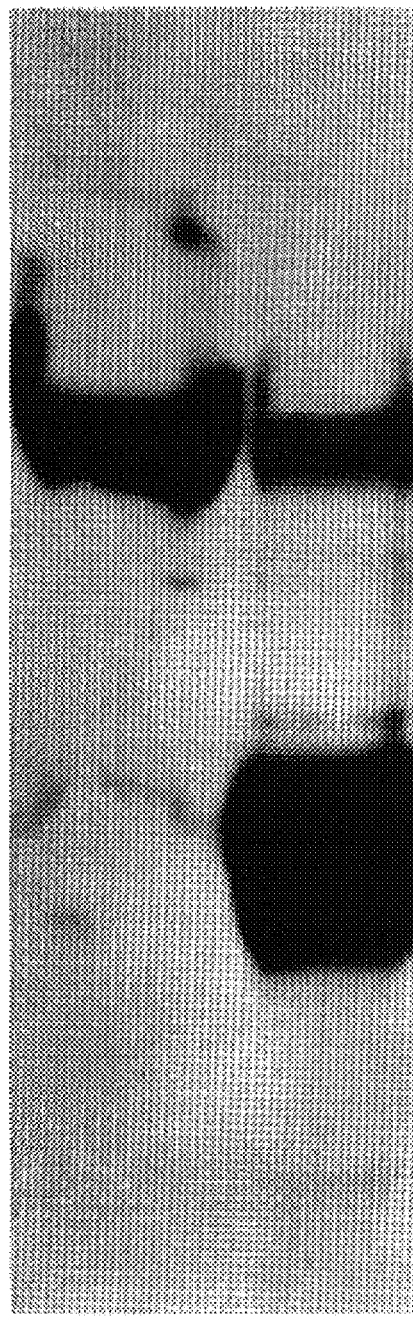

FIG. 6. Demonstration that monoclonal antibodies 7E11-C5 and 3F5.4G6 recognized an identical 120 kDa protein. PSMA from an LNCaP lysate was immunoprecipitated by monoclonal antibody 3F5.4G6, the proteins in the immunoprecipitate were separated on a SDS gel, transferred-to Immobilon P and probed in a Western blot with monoclonal antibody 7E11-C5. Lane 1=LNCaP lysate control and probed with 7E11-C5; Lane 2=3F5.4G6 immunoprecipitation.

Figure 7A:
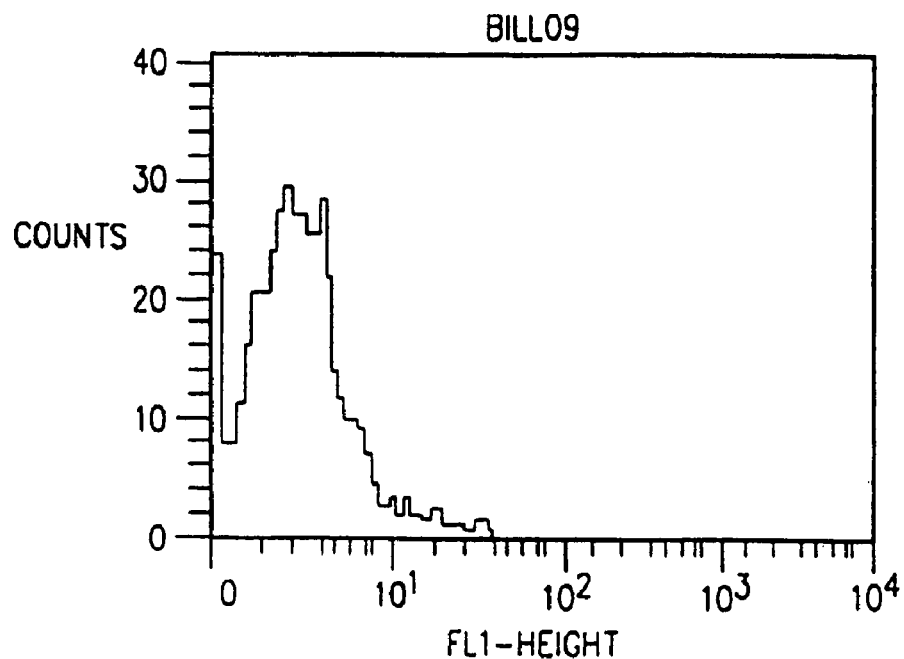
Figure 7B:
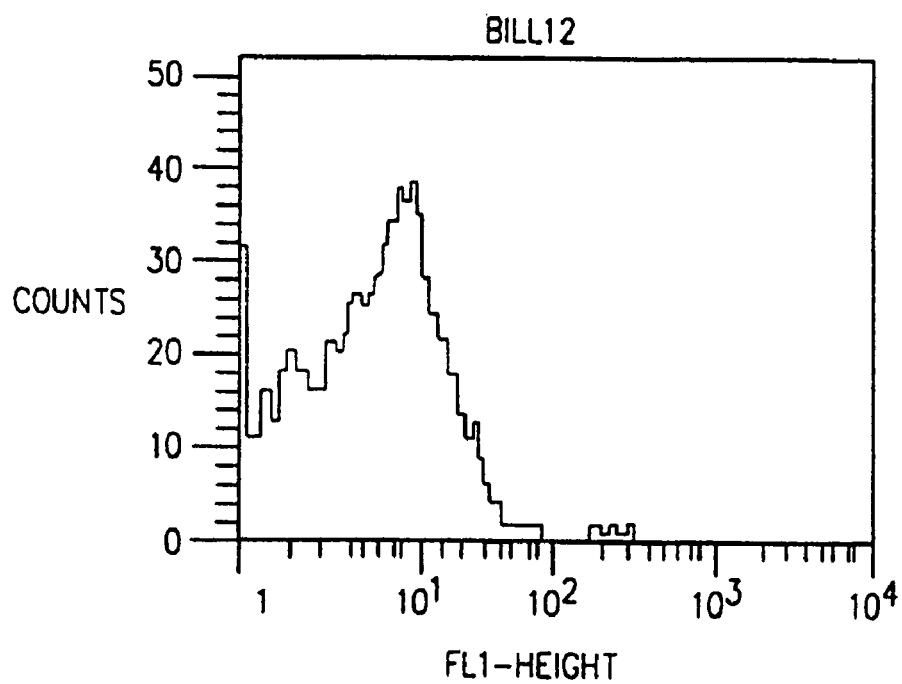

FIG. 7A & B Demonstration by FACS analysis of 3F5.4G6 monoclonal antibody recognition of live LNCaP cells illustrating antibody binding to the extracellular domain of PSMA. FIG. 7A represents control with no primary antibody; and FIG. 7B represents LNCaP cells incubated with 100 τg/ml of 3F5.4G6 prior to FACS analysis. The shift to the right indicates binding of the antibody to the live LNCap cells.

Figure 8:
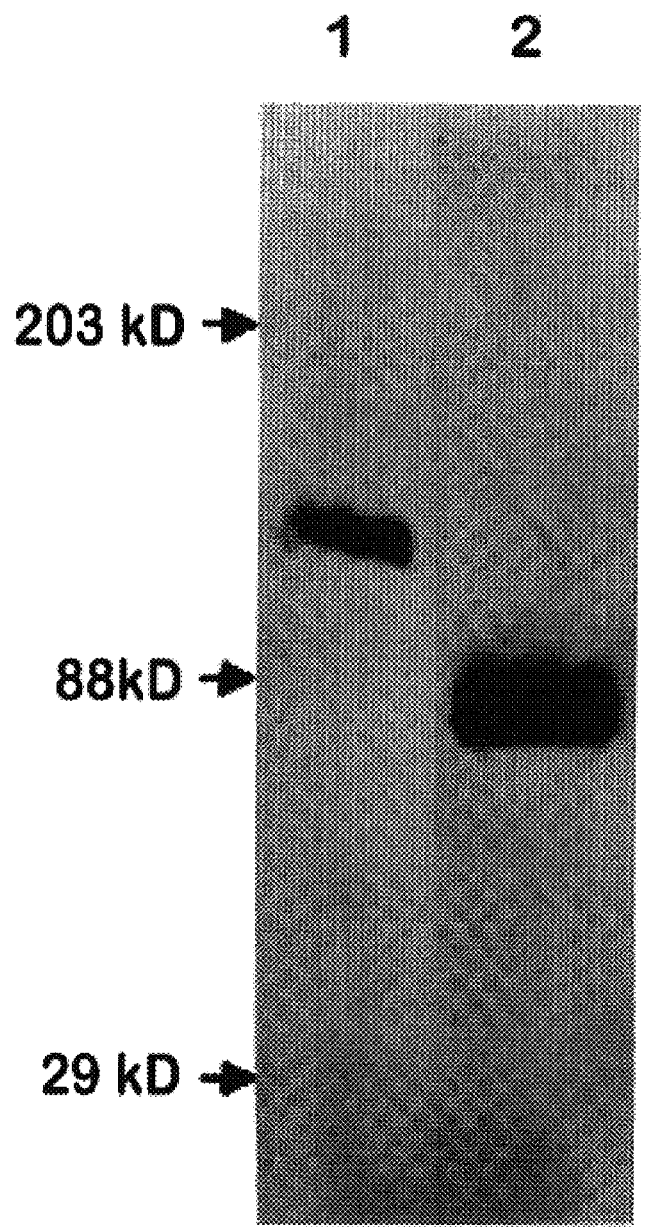

FIG. 8. Demonstration of the reactivity of monoclonal antibody 3F5.4G6 with PSM' isolated and purified from seminal fluid. Lane 1 is LNCaP lysate and Lane 2 is purified PSM' from seminal fluid. Proteins were separated on SDS polyacrylamide gels and transferred to Immobilon P paper and probed with monoclonal antibody 3F5.4G6 by Western blot procedures. The protein purified from seminal fluid and represented in Lane 2 is of molecular weight 90 kDa, which is likely to be a non-glycosylated or partially glycosylated product of PSM' having a molecular weight of 105-110 kDa.

Figure 9:
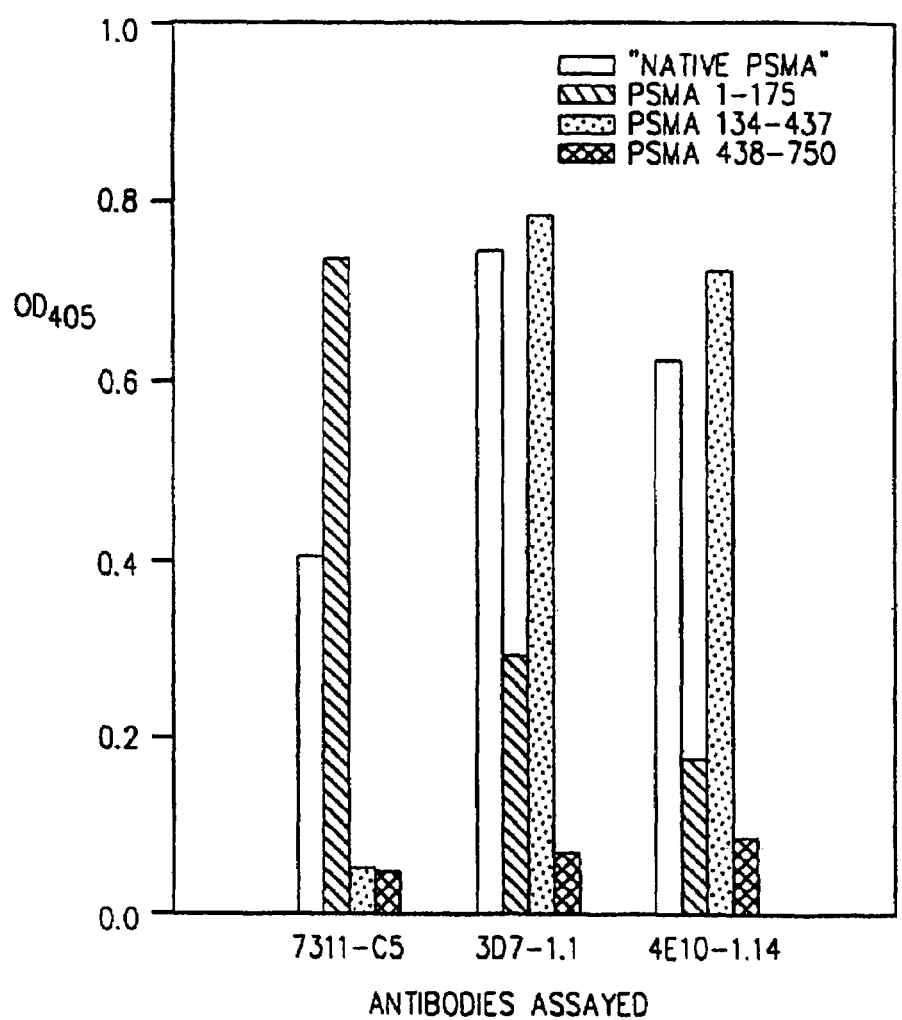

FIG. 9. Demonstration of the reactivity of monoclonal antibodies 3D7-1.1 and 4E10-1.14 with native PSMA and three PSMA fragments. Microtiter 96-well plates were coated with native PSMA or one of three bacterially-expressed polypeptide fragments of PSMA, and reacted with hybridoma supernatants in an ELISA. While all three tested antibodies showed comparable binding to native PSMA, 3D7-1.1 and 4E10-1.14 reacted strongly with a fragment corresponding to an epitope in the extracellular domain of PSMA.

Figure 10:
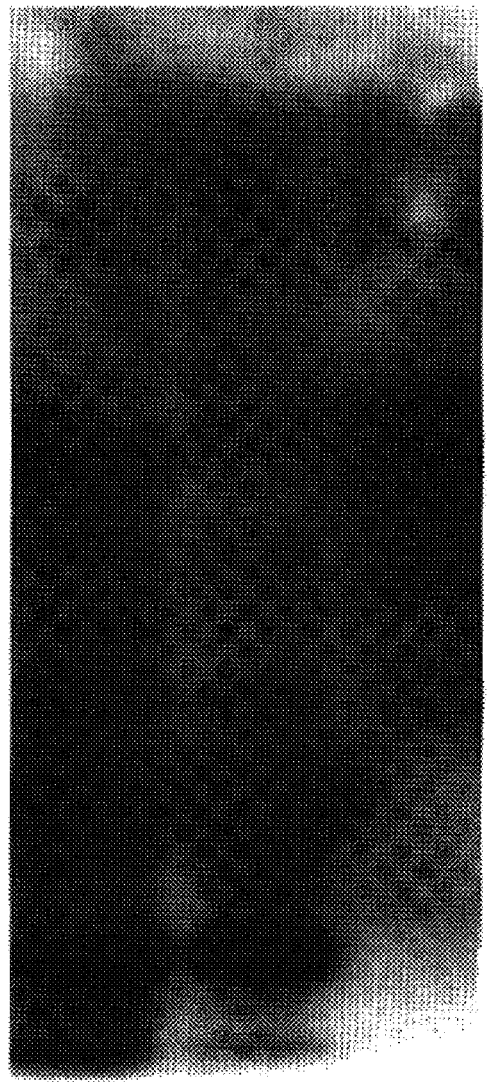

FIG. 10. Western blot analysis of PSMA using monoclonal antibodies 3D7-1.1. Lane 1=LNCaP lysate; Lane 2=PC-3 lysate; Lane 3=immunoaffinity-purified PSMA.

Figure 11:
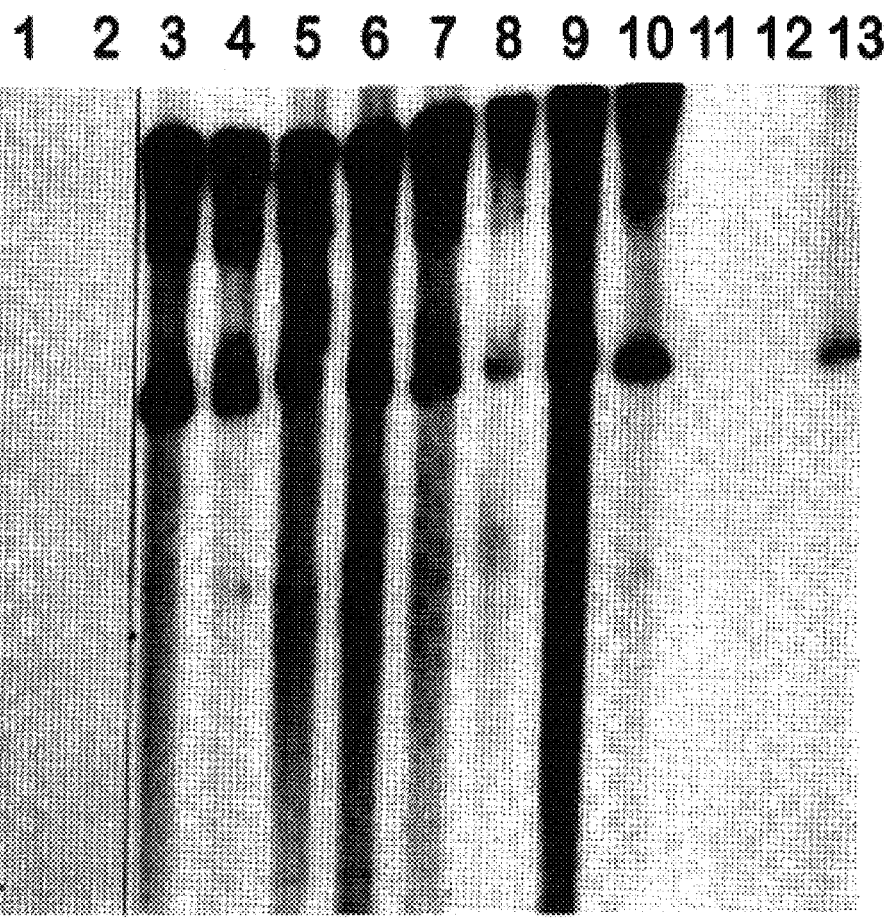
Figure 12C:
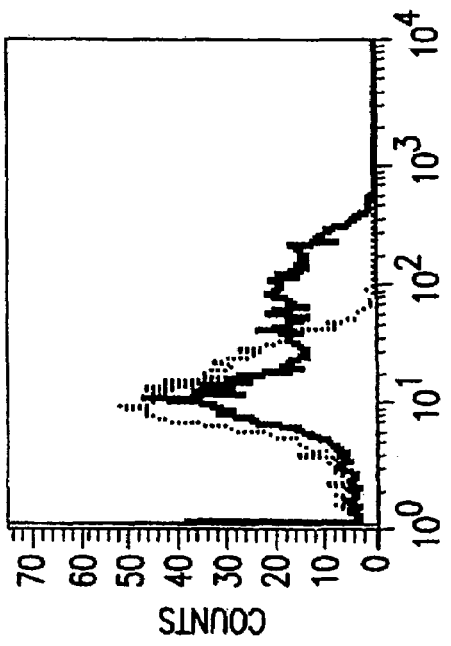
Figure 12D:
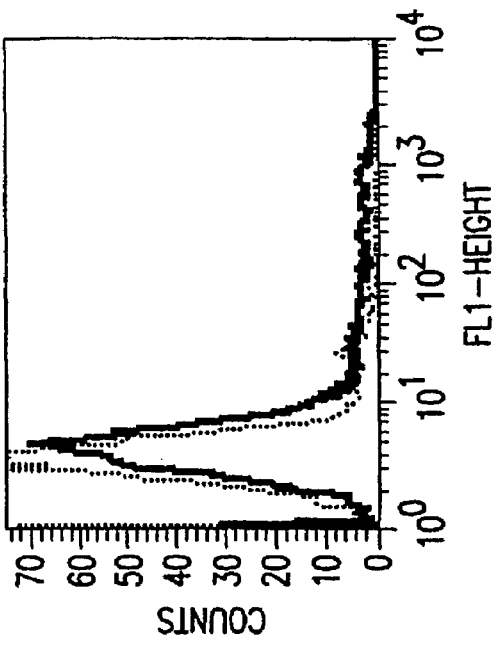
Figure 12A:
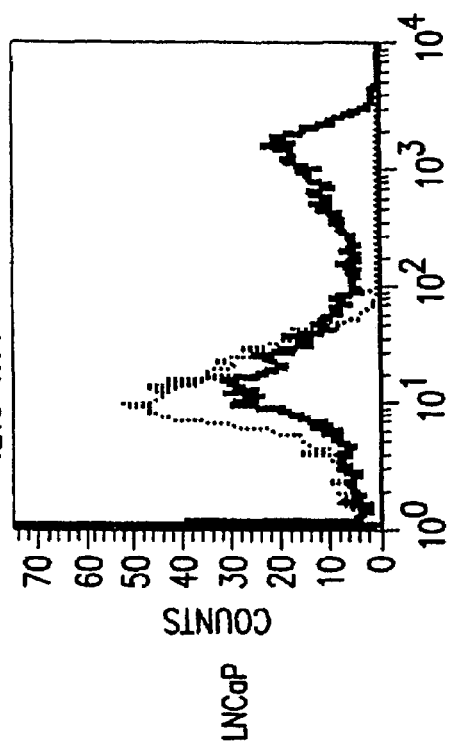
Figure 12B:
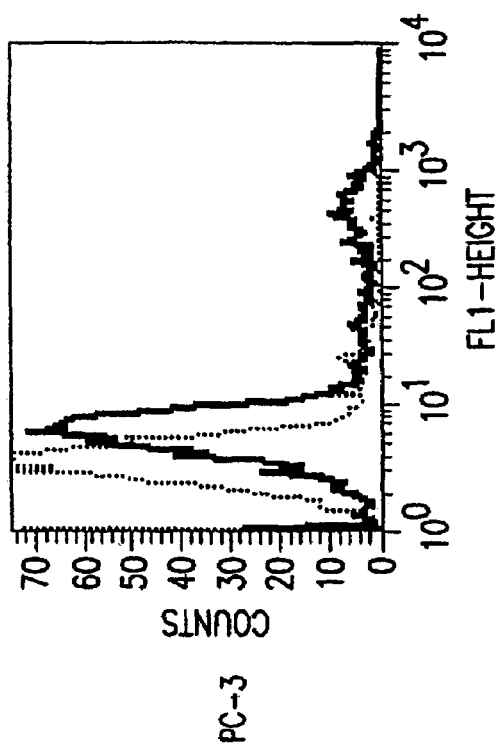

FIG. 11. Western blot analysis of full-length baculovirus-expressed PSMA. Recombinant PSMA was electrophoresed on SDS-PAGE gel, electroblotted and probed with various antibody preparations.
Lane 1=blank;
Lane 2=control medium (20% FCS in RPMI 1640;
Lane 3=3D7-1.1 monoclonal antibody;
Lane 4=3D7-1.2 monoclonal antibody;
Lane 5=3D7-1.3 monoclonal antibody;
Lane 6=3D7-1.7 monoclonal antibody;
Lane 7=3D7-2.7 monoclonal antibody;
Lane 8=4E10 (parent) monoclonal antibody;
Lane 9=4E10-1.3 monoclonal antibody;
Lane 10=4E10-1.14 monoclonal antibody;
Lane 11=blank;
Lane 12=blank;
Lane 13=7E11-C5 monoclonal antibody.

FIG. 12 A-D Demonstration by FACS analysis of 3D7-1.1 and 4E10-1.14 monoclonal antibody recognition of live LNCaP cells, illustrating antibody binding to the extracellular domain of PSMA. FIG. 12A represents LNCaP cells incubated with 4E10-1.14. FIG. 12B represents PC-3 cells incubated with 4E10-1.14. FIG. 12C represents LNCaP cells incubated with 3D7-1.1. FIG. 12D represents PC-3 cells incubated with 3D7-1.1. The different patterns in the shift to the right in FIG. 12A and 12C suggest that the two antibodies may recognize different epitopes of PSMA.

Figure 13:
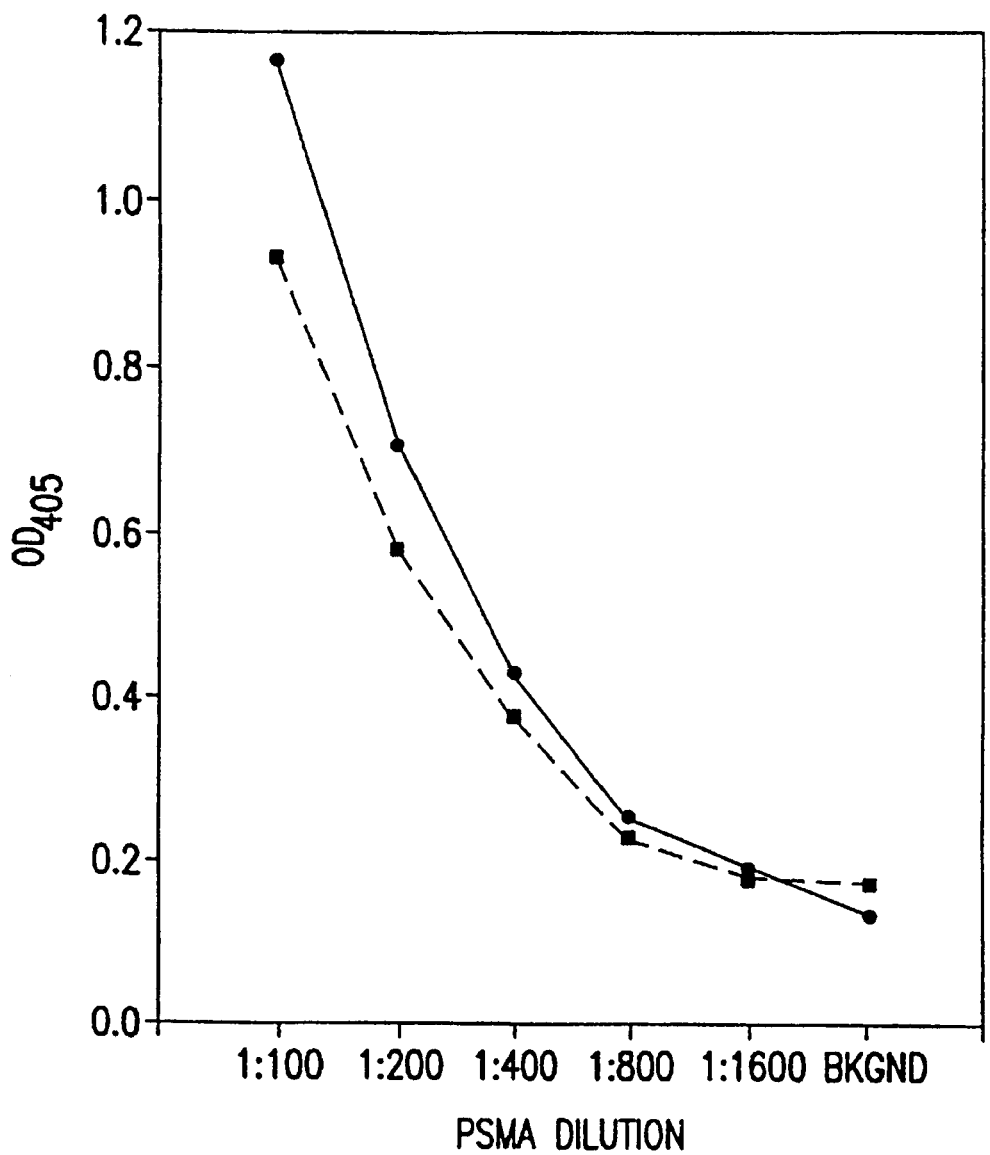

FIG. 13. Detection of PSMA by a two-site capture ELISA using two monoclonal antibodies to distinct epitopes of PSMA. Serially-diluted immunoaffinity-purified PSMA was added to 7E11-C5-coated 96 well plates and detected by incubating with 3D7-1.1 or 4E10-1.14 supernatants. The absorbance at 405 mm was measured in a microplate reader. The line with circles represents monoclonal antibody D7-1.1. The line with squares represents monoclonal antibody 4E10-1.14.

Figure 14:
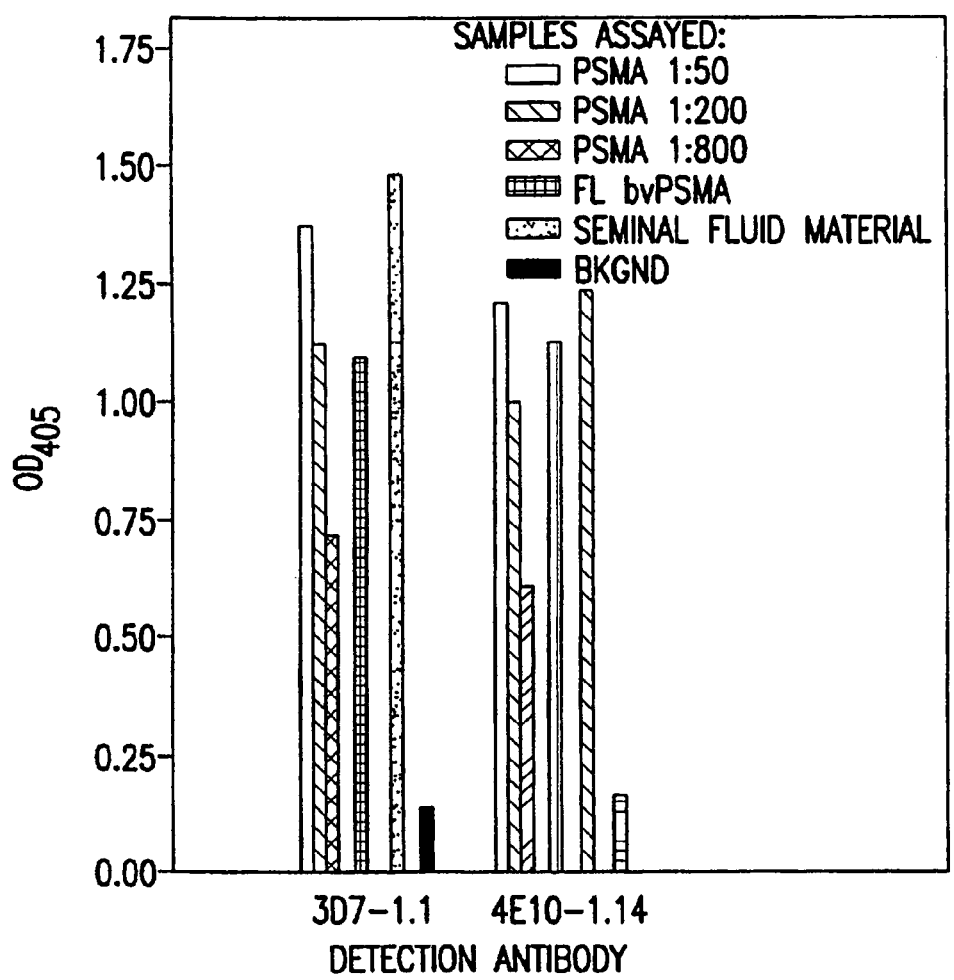

FIG. 14. Detection of PSMA in a variety of biological samples by a two-site capture ELISA using 3D7-1.1 and 4E10-1.14 monoclonal antibodies.

Figure 15:
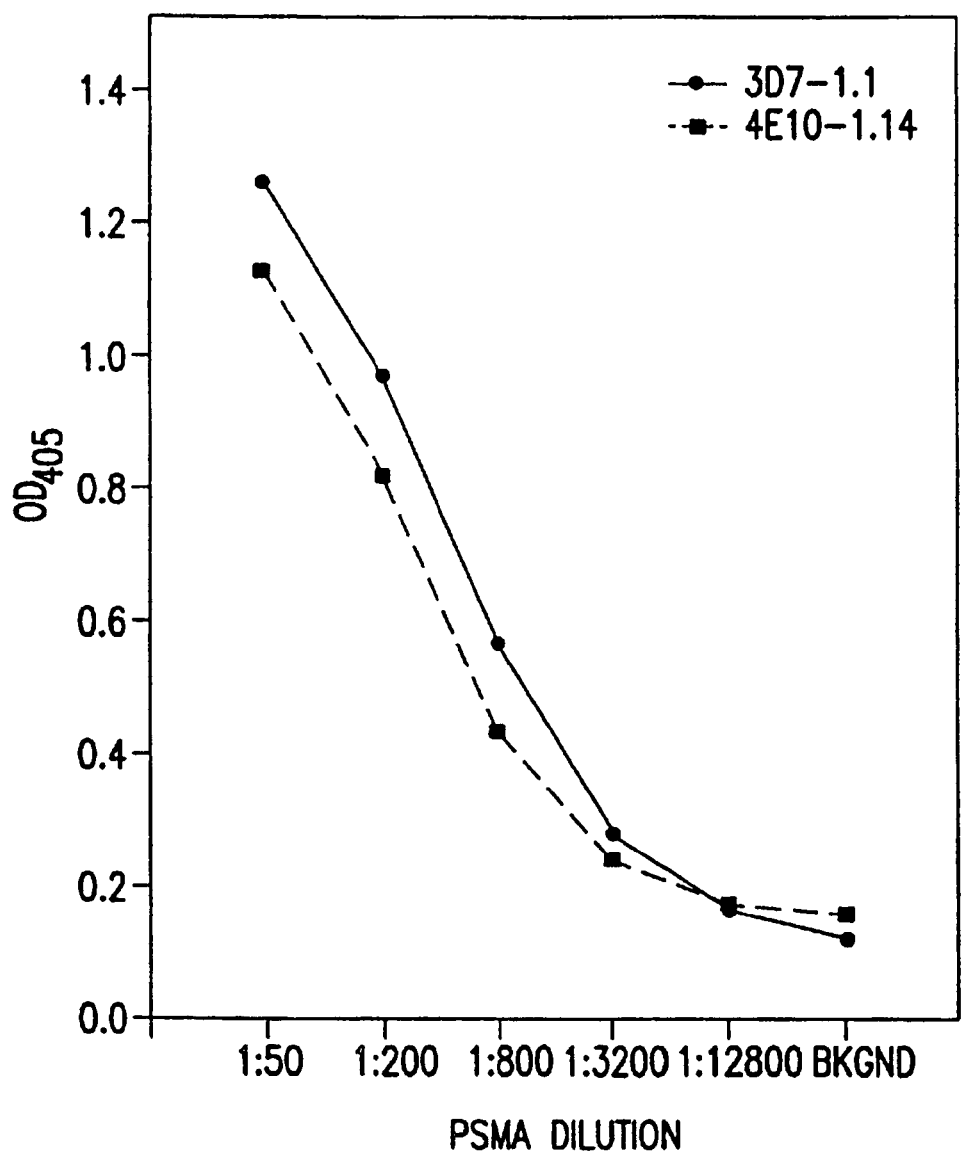

FIG. 15. Detection of immunoaffinity-purified PSMA serially diluted in normal human serum by a two-site capture ELISA using 307-1.1 and 4E10 1.14 monoclonal antibodies.

Figure 16:
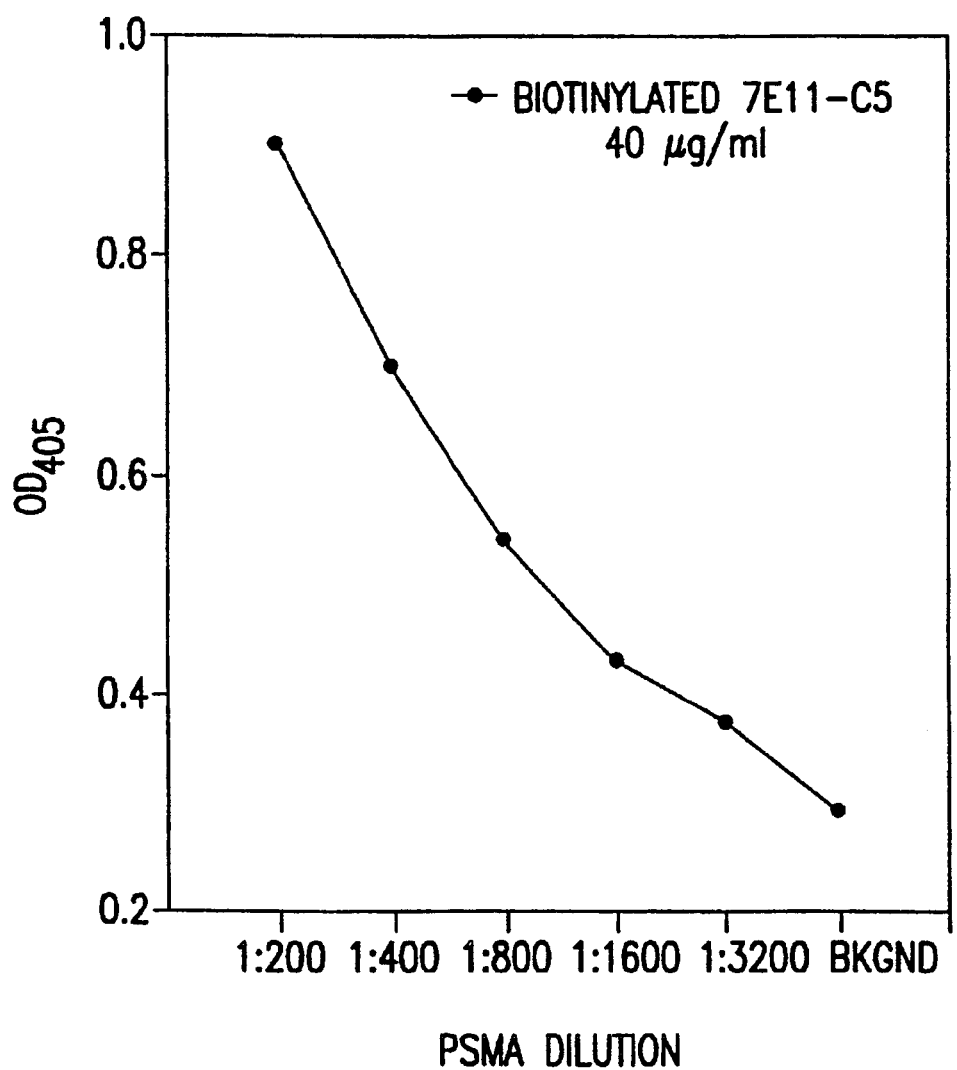

FIG. 16. Detection of PSMA by an alternate two-site capture ELISA. Serially diluted immunoaffinity purified PSMA was added to 3D7 1.1-coated 96 well plates and detected by incubating with biotinylated 7E11-C5 (40 τg/ml) followed by horse radish peroxidase conjugated streptavidin. The absorbance at 405 nm was measured in a microplate reader. 7E11-C5 was biotinylated using E-Z link Biotinylation kits (Pierce) according to manufacturer's instructions.

Figure 17:

FIG. 17. Western blot analysis of LNCaP cell lysate and various fractions of a semi-purified PSMA fragment (corresponding to amino acids 134 to 750 of full length PSMA, SEQ ID NO:2 expressed as a 1.9 kb insert in a baculovirus expression system) probed with tissue culture supernatant from the 4E10-1.14 hybridoma. The identification of the protein product from the 1.9 kb construct (amino acids 134-750 of PSMA, SEQ ID NO:2) is noted by the arrow.
Lane 1=Markers; Lane 2=LNCaP cell crude lysate; Lane 3=Viral pellet, i.e., 100,000×g pellet of lysed SF9 cells infected with baculovirus expressing 1.9 kb PSMA fragment; Lane 4=100,000×g supernatant fraction from lysed SF9 cells infected with baculovirus expressing 1.9 kb PSMA fragment; Lane 5=Flow thru of fraction shown in Lane 4 after passage through a Ni-NTA matrix; Lane 6=0.5M NaCl elution of Ni-NTA matrix; Lane 7=1M imidazole, pH 7.6 elution of Ni-NTA matrix; Lane 8=Flow thru of fraction shown in Lane 4 after passage through a Ni-NTA matrix; Lane 9=0.5M NaCl elution of Ni-NTA matrix; and Lane 10=1 M imidazole, pH 7.6 elution of Ni-NTA matrix. Also note in Lane 2 reactivity of 4E10-1.14 monoclonal antibody with native full length PSMA expressed in LNCaP cells.

Figure 18:
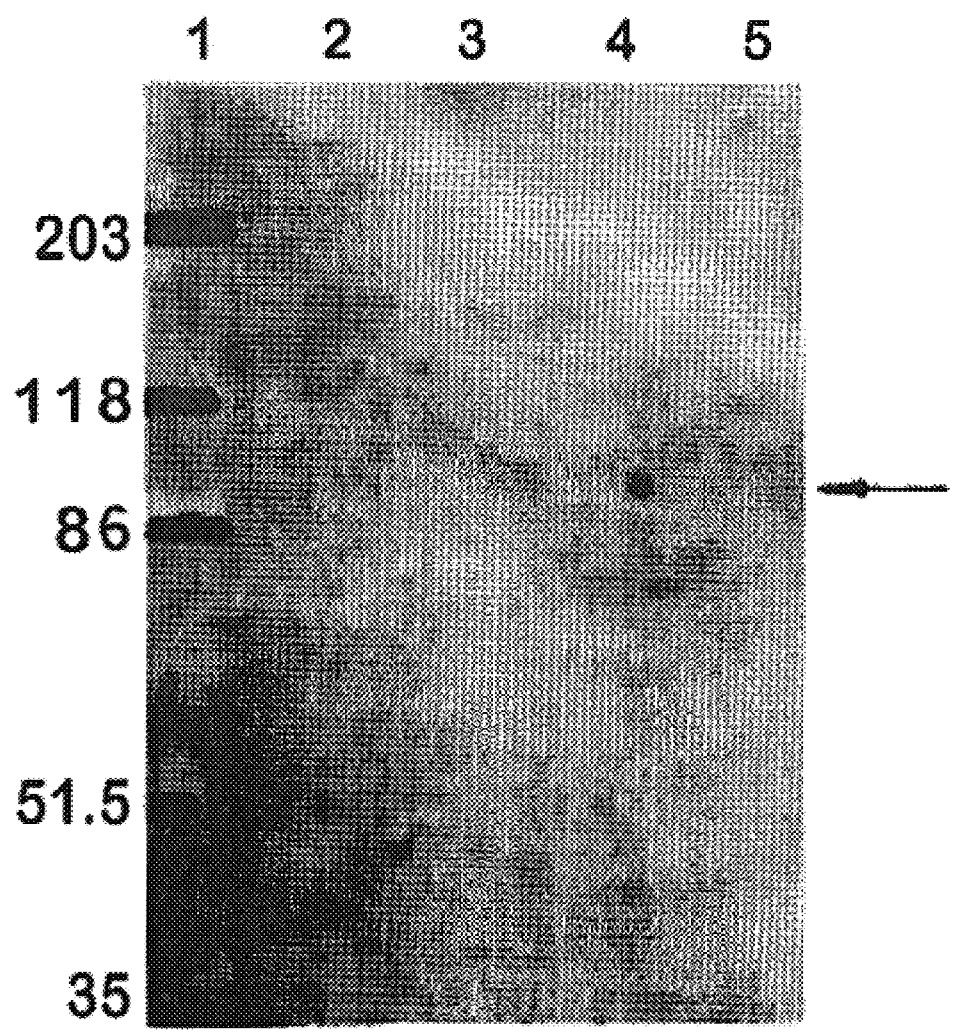

FIG. 18. Western blot of crude lysates of SF9 cells infected with a baculovirus containing either an irrelevant insert or a 1.9 kb insert encoding a portion of PSMA (amino acids 134-750 of full length PSMA, SEQ ID NO:2) probed with antibody 7E11-C5. Lanes 1,2=MW markers; Lane 3=irrelevant virus infected SF9 cell lysate; Lane 4=SF9 cell lysate; and Lane 5=1.9 kb PSMA insert containing virus infected SF9 lysate. Note that no 7E11-C5 positive bands were observed with any protein products present in SF9 cells or those infected with either virus.

Figure 19:
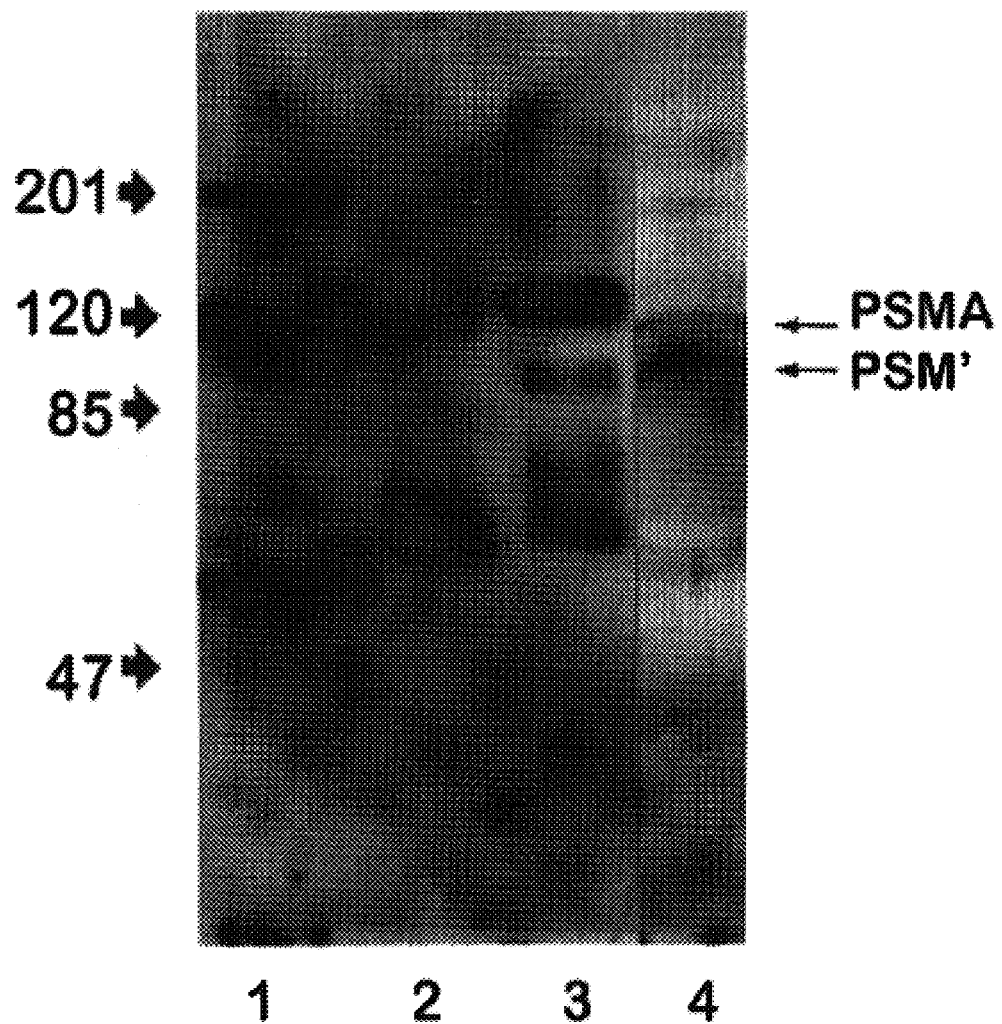

FIG. 19. Western blot of PSMA and PSM' obtained from LNCaP cells, human seminal fluid and human serum probed with monoclonal antibody 3D7-1.1. Lane 1=LNCaP cell lysate; Lane 2=7E11-C5 immunoaffinity purified PSMA from LNCaP cells; Lane 3=human seminal fluid; and Lane 4=human male serum. The positions of PSMA and PSM' are indicated.

Figure 20:
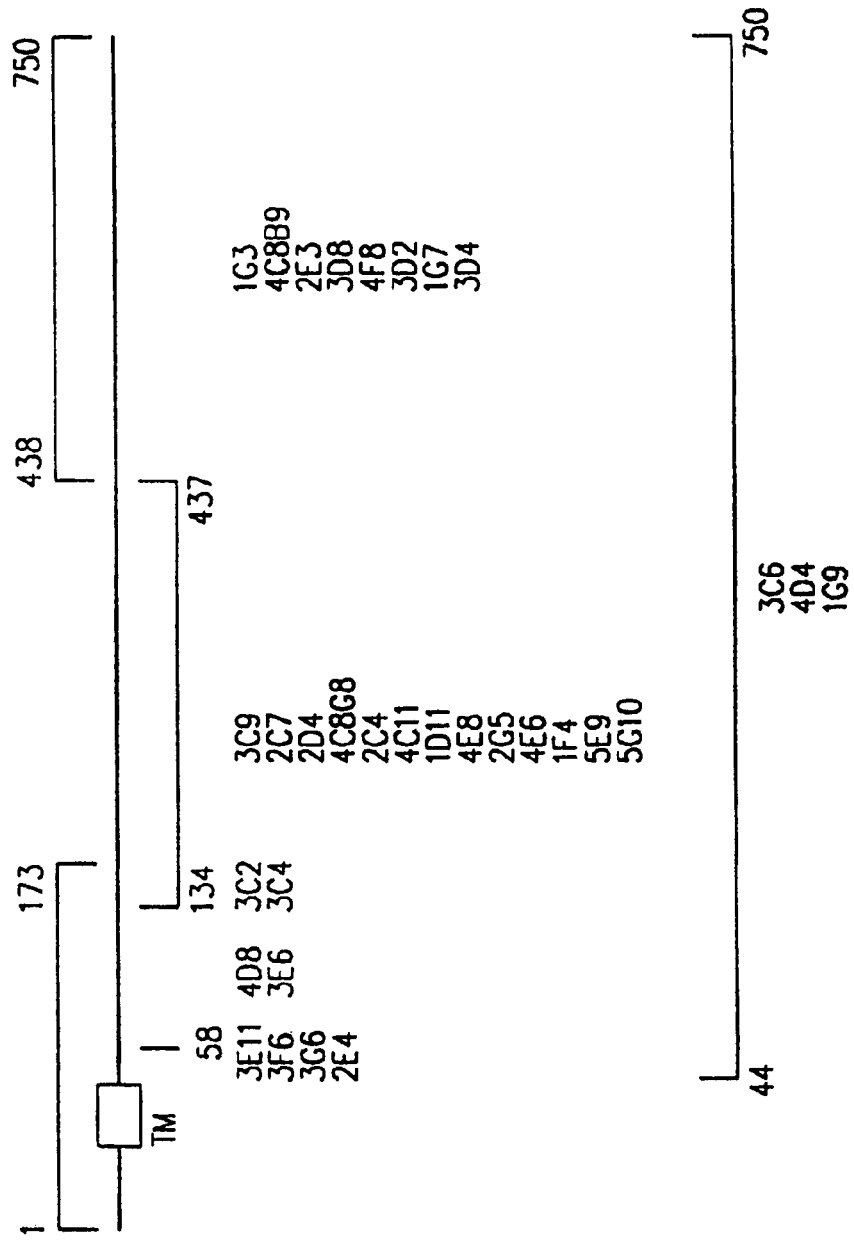

FIG. 20. Diagrammatic representation of PSMA and PSMA fragments expressed as bacterial fusion proteins. Full length PSMA is defined as amino acids 1 through 750 of SEQ ID NO:2. PSM' is missing the first 57 amino acids which also contains the transmembrane domain (TM, residues 20 through 43) of the protein. PSMA fragments utilized are composed of amino acids 1 through 173, amino acids 134 through 437, and amino acids 438 through 750, as indicated in the figure and in SEQ ID NO:2. The antibodies are listed below the region of the protein corresponding to the approximate location of their binding epitopes. The lower portion of the figure lists 3 antibodies which were found to bind only to native conformations of the protein and not denatured protein or protein fragments. Based on immunocytochemistry and flow cytometry experiments with live cells, these epitopes map to the extracellular domain, within amino acids 44 through 750 of SEQ ID NO:2.

5. DETAILED DESCRIPTION OF THE INVENTION

The present invention relates to monoclonal antibodies specific for the extracellular domain of PSMA, methods of using such antibodies and a truncated protein variant, PSM', identified by such antibodies. Although the specific procedures and methods described herein are exemplified using a C-terminal peptide, a PSMA-expressing tumor membrane preparation or purified PSMA to immunize mice, they are merely illustrative for the practice of the invention. Analogous procedures and techniques are equally applicable to a variety of animal hosts immunized against PSMA in the form of protein, peptides, cell surface antigen and crude membrane preparations.

5.1. Hybridoma Cell Lines and Antibody Production

In a specific embodiment by the way of example in Section 6, infra, a synthetic peptide derived from the C-terminal region of PSMA was used as an immunogen. The results show that one antibody designated 3F5.4G6 binds to the extracellular domain of PSMA, which is exposed on the cell surface of live prostate cancer cells and in the sera of prostate cancer patients. Additionally, working examples in Sections 7 and 8, infra, demonstrate the production of additional monoclonal antibodies directed to the extracellular domain of PSMA following immunization of animals with a PSMA-expressing tumor membrane preparation. In this connection, cancer cells such as LNCaP that express PSMA, host cells transfected with PSMA coding sequence, purified PSMA, PSM' or PSMA extracellular domain peptides may be used as immunogen to elicit an immune response in animal hosts for the generation of monoclonal antibodies specific for the extracellular domain of PSMA.

Somatic cells with the potential for producing antibody and, in particular B lymphocytes, are suitable for fusion with a B-cell myeloma line. Those antibody-producing cells that are in the dividing plasmablast stage fuse preferentially. Somatic cells may be obtained from the lymph nodes, spleens and peripheral blood of antigen-primed animals, and the lymphatic cells of choice depend to a large extent on their empirical usefulness in the particular fusion system. Once-primed or hyperimmunized animals can be used as a source of antibody-producing lymphocytes. Mouse lymphocytes give a higher percentage of stable fusions with the mouse myeloma lines described below. Of these, the BALB/c mouse is preferred. However, other mouse strains, rabbit, hamster, sheep and frog may also be used as hosts for preparing antibody-producing cells. As reviewed by Goding (in Monoclonal Antibodies: Principles and Practice, 2d ed., pp. 60-61, Orlando, Fla., Academic Press, 1986), use of rat lymphocytes may provide several advantages.

Alternatively, human somatic cells capable of producing antibody, specifically B lymphocytes, are suitable for fusion with myeloma cell lines. While B lymphocytes from biopsied spleens, tonsils or lymph nodes of individual may be used, the more easily accessible peripheral blood B lymphocytes are preferred. The lymphocytes may be derived from patients with diagnosed prostate carcinomas. In addition, human S cells maybe directly immortalized by the Epstein-Barr virus (Cole et al., 1995, Monoclonal Antibodies and Cancer Therapy, Alan R. Liss, Inc., pp. 77-96).

Myeloma cell lines suited for use in hybridoma-producing fusion procedures preferably are non-antibody-producing, have high fusion efficiency, and enzyme deficiencies that render them incapable of growing in certain selective media which support the growth of the desired hybridomas. Examples of such myeloma cell lines that may be used for the production of fused cell hybrids of the invention, include P3-X63/Ag8, X63-Ag8.653, NS1/1.Ag 4.1, Sp210-Ag14, FO, NSO/U, MPC-11, MPC11-X45-GTG 1.7, S194/5XX0 Bul, all derived from mice; R210.RCY3, Y3-Ag 1.2.34 IR983F and 4B210 derived from rats and U-266, GM1500-GRG2, LICR-LON-HMy2, UC729-6, all derived from humans (Goding in Monoclonal Antibodies: Principles and Practice, 2d ed., pp. 65-66, Orlando, Fla., Academic Press, 1986; Campbell, in Monoclonal Antibody Technology, Laboratory Techniques in Biochemistry and Molecular Biology Vol. 13, Burden and Von Knippenberg, eds. pp. 75-83, Amsterdam, Elseview, 1984).

Methods for generating hybrids of antibody-producing spleen or lymph node cells and myeloma cells usually comprise mixing somatic cells with myeloma cells in a 2:1 proportion (though the proportion may vary from about 20:1 to about 1:1, respectively, in the presence of an agent or agents (chemical or electrical) that promote the fusion of cell membranes. It is often preferred that the same species of animal serve as the source of-the somatic and myeloma cells used in the fusion procedure. Fusion methods have been described by Kohler and Milstein (1975, Nature 256: 495-497; 1976, Eur. J. Immunol. 6:511-519), and by Gefter et al. (1977, Somatic Cell Genet. 3:231-236). The fusion-promotion agents used by those investigators were Sendai virus and polyethylene glycol (PEG), respectively. Fusion methods reviewed by Goding (1986, in Monoclonal Antibodies: Principles and Practice, 2d ed., pp. 71-74, Orlando, Fla., Academic Press), including the above as well as electrically induced fusion are also suitable to generate monoclonal antibodies of the invention.

Fusion procedures usually produce viable hybrids at very low frequency, about $1\times10^{-6}$ to $1\times10^{-8}$ somatic cells. Because of the low frequency of obtaining viable hybrids, it is essential to have a means to select fused cell hybrids from the remaining unfused cells, particularly the unfused myeloma cells. A means of detecting the desired antibody-producing hybridomas among the other resulting fused cell hybrids is also necessary.

Generally, the fused cells are cultured in selective media, for instance HAT medium containing hypoxanthine, aminopterin and thymidine. HAT medium permits the proliferation of hybrid cells and prevents growth of unfused myeloma cells which normally would continue to divide indefinitely. Aminopterin blocks de novo purine and pyrimidine synthesis by inhibiting the production of tetrahydrofolate. The addition of thymidine bypasses the block in pyrimidine synthesis, while hypoxanthine is included in the media so that inhibited cells synthesize purine using the nucleotide salvage pathway. The myeloma cells employed are mutants lacking hypoxanthine phosphoribosyl transferase (HPRT) and thus cannot utilize the salvage pathway. In the surviving hybrid, the B lymphocyte supplies genetic information for production of this enzyme. Since B lymphocytes themselves have a limited life span in culture (approximately two weeks), the only cells which can proliferate in HAT media are hybrids formed from myeloma and spleen cells.

To facilitate screening of antibody secreted by the hybrids and to prevent individual hybrids from overgrowing others, the mixture of fused myeloma and B lymphocytes is diluted in HAT medium and cultured in multiple wells of microtiter plates. In two to three weeks, when hybrid clones become visible microscopically, the supernatant fluid of the individual wells containing hybrid clones is assayed for specific antibody. The assay must be sensitive, simple and rapid. Assay techniques include radioimmunoassays, enzyme immunoassays, cytotoxicity assays, plaque assays, dot immunobinding assays, and the like.

Once the desired fused cell hybrids have been selected and cloned into individual antibody-producing cell lines, each cell line may be propagated in either of two standard ways. A sample of the hybridoma can be injected into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can be tapped to provide monoclonal antibodies in high concentration. Alternatively, the individual cell lines may be propagated in vitro in laboratory culture vessels; the culture medium, also containing high concentrations of a single specific monoclonal antibody, can be harvested by decantation, filtration or centrifugation.

In addition to the hybridoma technology, monoclonal antibodies specific for the extracellular domain of PSMA may be produced by other methods well known in the art. For example, molecular approaches using phage display technology may be used to express antibody variable regions that bind PSMA (U.S. Pat. Nos. 5,223,409; 5,403,484 and 5,571,698).

Monoclonal antibodies or purified fragments of the monoclonal antibodies having at least a portion of an antigen binding region, including such as Fv, F(ab')$_2$, Fab fragments (Harlow and Lane, 1988, Antibody, Cold Spring Harbor), single chain antibodies (U.S. Pat. No. 4,946,778), chimeric or humanized antibodies (Morrison et al., 1984, Proc. Natl. Acad. Sci. USA 81:6851; Newuberger et al., 1984 Nature 81:6851) and complementarity determining regions (CDR) may be prepared by conventional procedure. Purification of the antibodies or fragments can be accomplished by a variety of methods known to those of skill including, precipitation by ammonium sulfate or sodium sulfate followed by dialysis against saline, ion exchange chromatography, affinity or immunoaffinity chromatography as well as gel filtration, zone electrophoresis, etc. (see Goding in, monoclonal Antibodies: Principles and Practice, 2d ed., pp 104-126, Orlando, Fla., Academic Press).

5.2. Characterization of Monoclonal Antibodies and PSM'

Using techniques described generally in Section 5.1 supra and illustrated in the Sections 6-8, infra, thirty-five hybridoma cell lines were selected because of their production of monoclonal antibodies specific for the extracellular domain of PSMA. The present invention encompasses the monoclonal antibodies exemplified in Sections, 6, 7 and 8, infra, as well as other monoclonal antibodies that bind specifically to the extracellular domain of PSMA and PSM', particularly including any antibodies that competitively inhibit the binding of any one or more of the aforementioned antibodies to PSMA as assessed in an enzyme immunoassay, a radioimmunoassay or any other competitive binding immunoassay.

Antibody 3F5.4G6 is an IgM isotype antibody that binds specifically to PSMA expressed in prostate cancer cell lysates and on the cell surface of prostate cancer cells, as well as in sera obtained from prostate carcinoma patients. In addition, 3F5.4G6 also binds specifically to PSM'. The 3F5.4G6-reactive PSMA epitope is extracellular, C-terminal and distinct from that recognized by 7E11-C5 (Horoszewicz et al., Anti-cancer Res. 7:927-936) which is membrane associated in the cytoplasm of the cell. Antibodies 3D7-1.1 and 4E10-1.14 are also IgM antibodies and bind to PSMA expressed in prostate cancer cell lysates and on the cell surface. These antibodies may be used to detect both primary prostate cancer and metastatic tumors such as bone metastases of prostate cancer. In addition, thirty-two antibodies of the IgG isotype have been generated and they are specific for epitopes throughout the extracellular domain of PSMA. Antibodies of the IgG isotype activate complement-mediated cytolysis and bind to phagocytic cells via their Fc region. In addition, their smaller size and stability may allow better penetration than IgM in tissues in vivo.

During the development of an antibody response, antibody-producing cells first secrete the IgM isotype which eventually switches to IgG. Such class switching events occur by DNA rearrangement of constant region genes so that the same antigen specificity is retained. The different antibody isotypes possess different effector functions. For example, IgM and all IgG subclasses except IgG4 can fix complement upon antigen binding. In contrast, IgE binds to mast cells in an allergic reaction to trigger histamine release.

Hybridoma cell lines also produce class switch variants during long-term culture. In particular, monoclonal antibodies switching from IgM to IgG or IgG$_1$ to IgG$_{2a}$ have been selected for their higher affinity for protein A, which facilitates their purification. Any class switch variant may be selected for a particular desirable effector function (Spira et al., 1985, in Hybridoma Technology in the Biosciences and Medicine, ed. Springer, pp. 77-88, Plenum Press, NY; Harlow and Lane, 1988 Antibodies, Cold Spring Harbor Laboratory). In the case of the exemplified antibodies, since a few of them are of IgM isotype, it is desirable to also select for IgG variants that possess the same antigen specificity, which may be more useful for certain purposes in vitro or in vivo. The present invention encompasses IgG variants of the monoclonal antibodies of the invention, including 3F5.4G6, 3D7-1.1 and 4E10-1.14.

Sections 6-8, infra, show that the exemplified antibodies recognize a 120 kDa molecular weight protein. In particular, most of these antibodies also recognize a 105-110 kDa molecular weight protein in prostate tumor cell lysates. While the 120 kDa protein is also recognized by antibody 7E11-C5, the lower molecular weight protein is detected only by the antibodies of the invention. Therefore, the 105-110 kDa protein represents the product of a mRNA known as PSM'. However, prior to the present invention, a PSM' protein was never reported; and it was thought to be an untranslated mRNA. Since the amino acid sequence of PSM' is presumed to lack the cytoplasmic and transmembrane regions of PSMA as deduced from its RNA sequence, it is consistent that 7E11-C5 would not react with this product because of its specificity for an intracellular epitope. In contrast, antibodies specific for the extracellular domain of PSMA also recognize PSM'.

5.3. Coding Sequences of PSMA-Specific Monoclonal Antibodies

In another embodiment of the invention, the exemplified hybridoma cell lines may be used to produce compositions comprising an antigen binding site or antibody variants which combine the murine variable or hypervariable regions with the human constant region or constant and variable framework regions, i.e., chimeric or humanized antibodies as well as humanized antibodies that retain only the antigen-binding CDRs from the parent antibody in association with human framework regions (see, Waldmann, 1991, Science 252: 1657, 1662, particularly 1658-59 and references cited therein). Such chimeric or humanized antibodies retaining binding specificity of the murine antibody are expected to have reduced immunogenicity when administered in vivo for diagnostic, prophylactic or therapeutic applications according to the invention.

In yet other embodiments, the invention encompasses the use of the hybridoma cell lines as a source of DNA or mRNA encoding for the rearranged, activated immunoglobulin genes, which may be isolated, cloned by known recombinant DNA techniques and transferred to other cells for the production of antigen binding fragments specific for the extracellular domain of PSMA. By isolating rearranged DNA or preparing cDNA from the messenger RNA of the hybridoma cell line of the invention, a sequence free of introns may be obtained.

To illustrate, and not by way of limitation, an immunoexpression library can be prepared and screened for antibody binding fragments for PSMA and PSM' as follows (See, Huse et al., 1989, Sci. 246:1275-1281; Mullinax et al., 1990, Proc. Natl Acad. Sci. USA 87:8045-8099). Total RNA can be purified (e.g., using commercially available kits) and converted to cDNA using an oligo (dT) primer for the light (L) chain and a specific primer for the heavy (H) chain using reverse transcriptase. Polymerase chain reaction (PCR) amplification of the immunoglobulin H and L chain sequences can be done separately with sets of primer pairs. Upstream primers can be designed to hybridize to partially conserved sequences in the leader and/or framework regions of $V_H$ or $V_L$ and downstream primers can be designed to hybridize to constant domain sequences. Such primers would preserve full length L chain and provide H chains corresponding to the Fd of IgG and conserving the H-L disulfide bonds. The PCR amplified L and H DNA fragments are then digested and separately ligated into H and L chain vectors. Such vectors contain a pelB leader sequence, a ribosome binding site and stop codons. Suitable λ phage vectors for expression in *E. coli* can be prepared from commercially available vectors (ImmunoZAP L, ImmunoZAP H; Stratacyte, La Jolla, Calif.). The ligated recombinant phage DNA is incorporated into bacteriophage with in vitro packaging extract and used to infect *E. coli*. The immunoexpression library thus created is screened for antigen binding fragments using PSMA, PSM' or a specific peptide thereof. Positive clones can be screened and identified as described by Mullinax et al. (supra).

5.4. Uses of PSMA Extracellular Domain-Specific Antibodies and Antibody Compositions Although the specific procedures and methods described herein are exemplified using the monoclonal antibodies of the invention, they are merely illustrative for the practice of the invention. Purified fragments of the monoclonal antibodies having at least a portion of the antigen-binding region, including Fv, F(ab')2, Fab fragments, single chain antibodies, chimeric or humanized antibodies or CDRs can be used in the procedures and methods described below according to the present invention.

5.4.1 Immunohistological and Immunocytological Applications

Monoclonal antibodies of the present invention can be used to detect prostate carcinoma cells in histological and cytological specimens, and, in particular, to distinguish malignant tumors from normal tissues and non-malignant tumors. Tissue specimens may be stained by the antibodies and their binding detected by a second antibody conjugated to a label such as peroxidase, fluorescein, alkaline phosphatase, and the like.

In addition, immunofluorescence techniques can use the monoclonal antibodies of the present invention to examine human tissue, cell and bodily fluid specimens. In a typical protocol, slides containing cryostat sections of frozen, unfixed tissue biopsy samples or cytological smears are air dried, formalin or acetone fixed, and incubated with the monoclonal antibody preparation in a humidified chamber at room temperature.

The slides are then washed and further incubated with a preparation of antibody directed against the monoclonal antibody, usually some type of anti-mouse immunoglobulin if the monoclonal antibodies used are derived from the fusion of a mouse spleen lymphocyte and a mouse myeloma cell line. This anti-mouse immunoglobulin is tagged with a compound, for instance rhodamine or fluorescein isothiocyanate, that fluoresces at a particular wavelength. The staining pattern and intensities within the sample are then determined by fluorescent light microscopy and optionally photographically recorded.

As yet another alternative, computer enhanced fluorescence image analysis or flow cytometry can be used to examine tissue specimens or exfoliated cells, i.e., single cell preparations from aspiration biopsies of prostate tumors using the monoclonal antibodies of the invention. The monoclonal antibodies of the invention are particularly useful in quantitation of live tumor cells, i.e., single cell preparations from aspiration biopsies of prostate tumors by computer enhanced fluorescence image analyzer or with a flow cytometer. The antibodies of the invention are particularly useful in such assays to differentiate benign from malignant prostate tumors since PSMA to which the monoclonal antibodies bind is expressed in increased amounts by malignant tumors. The percent PSMA positive cell population, alone or in conjunction with determination of the DNA ploidy of these cells, may, additionally, provide very useful prognostic information by providing an early indicator of disease progression.

In yet another alternative embodiment, the monoclonal antibodies of the present invention can be used in combination with other known prostate antibodies to provide additional information regarding the malignant phenotype of a prostate carcinoma.

5.4.2 Immunoserological Applications

The use of the monoclonal antibodies of the invention can be extended to the screening of human biological fluids for the presence of the specific antigenic determinants recognized. In vitro immunoserological evaluation of biological fluids withdrawn from patients thereby permits non-invasive diagnosis of cancers. By way of illustration, human bodily fluids such as prostatic fluid, seminal fluid, whole blood, serum or urine can be taken from a patient and assayed for the specific epitope, either as released antigen or membrane-bound on cells in the sample fluid, using monoclonal antibodies specific for the extracellular domain of PSMA and PSM, in standard radioimmunoassays or enzyme-linked immunoassays, competitive binding enzyme-linked immunoassays, dot blot or Western blot, or other assays known in the art.

In addition, a more sensitive diagnostic assay for PSMA or PSM' protein can be developed through the use of monoclonal antibodies directed to non-overlapping epitopes on PSMA and PSM'. Antibodies specific for opposite ends of PSMA such as 7E11-C5 and the antibodies of the invention are particularly suitable for use in such an assay. In this regard, one antibody may be anchored to a substrate to capture PSMA or PSM' in a biological fluid, while the other antibody is used to detect the antibody-bound antigen. Also, since the expression of PSMA and PSM' is increased in prostate cancer and normal prostate tissues, respectively, antibodies that distinguish these two forms may be used to provide a more accurate way to monitor tumor regression versus progression, following treatment. Since most antibodies of the invention recognize both forms, but 7E11-C5 only binds to PSMA, these antibodies may be used in conjunction to determine the precise levels of each form in a patient, thereby correlating their amounts with tumor burden. For example, 7E11-C5 may be used as an anchored antibody in a two-site capture assay, and any one of the other extracellular domain-specific antibodies may be used as a detection antibody to quantitate PSMA. On the other hand, any combination of two of the PSMA extracellular domain-specific antibodies may be used in a similar two-site capture assay, to specifically measure total PSM' plus PSMA concentrations. A simple subtraction of PSMA from total PSMA and PSM' specifically quantitates PSM'.

In addition to the detection of extracellular domain PSMA and PSM' by a monoclonal antibody in tissues and bodily fluids, NAALADase enzyme activity measurements can be utilized to quantitate extracellular domain PSMA and/or PSM' in tissues and/or bodily fluids.

For example, tissue levels can be determined by detergent solubilizing homogenizing tissues, pelleting the insoluble material by centrifugation and measuring the NAALADase activity in the remaining supernatant. Likewise, the NAALADase activity in bodily fluids can also be measured by first pelleting the cellular material by centrifugation and performing a typical enzyme assay for NAALADase activity on the supernatant.

NAALADase assay protocols taking advantage of antibody binding specificities can also be applied. For example, solid surfaces coated with either 7E11-C5, or the antibodies of the invention could be used to capture the PSMA or PSM' protein for detection using a NAALADase enzyme assay. Thus, this may be used to differentially detect and quantitate full length PSMA protein and PSM' in a specimen given that an extracellular domain-specific antibody binds to both PSMA and PSM', whereas 7E11-C5 would only bind to PSMA.

More convenient NAALADase enzyme assays, taking advantage of the reaction properties of glutamate dehydrogenase may also be applied (Frieden, 1959, J. Biol. Chem., 234:2891). In this assay, the reaction product of the NAALADase enzyme is glutamic acid. This is derived from the enzyme catalyzed cleavage of N-acetylaspartylglutamate to yield N-acetylaspartic acid and glutamic acid. Glutamic acid, in a NAD(P)$^+$ requiring step, yields 2-oxoglutarate plus NAD(P)H in a reaction catalyzed by glutamate dehydrogenase. Progress of the reaction can easily and conveniently be measured by the change in absorbance at 340 nm due to the conversion of NAD(P)$^+$ to NAD(P)H. Thus, improvements to the assay of NAALADase activity applicable to a solid phase format with immobilized capture antibodies can be achieved. In this way, multiple assays can be conducted simultaneously in a microplate reader based upon the absorbance change at 340 nm before and after addition of NAD$^+$ or NADP$^+$. It would not be restricted to solid phase assays, as solution assays of, e.g., serum would also be possible with this type of NAALADase assay.

Kits containing the monoclonal antibodies of the invention or fragments thereof can be prepared for in vitro diagnosis, prognosis and/or monitoring prostate carcinoma by the immunohistological, immunocytological and immunoserological methods described above. The components of the kits can be packaged either in aqueous medium or in lyophilized form. When the monoclonal antibodies (or fragments thereof) are used in the kits in the form of conjugates in which a label moiety is attached, such as an enzyme or a radioactive metal ion, the components of such conjugates can be supplied either in fully conjugated form, in the form of intermediates or as separate moieties to be conjugated by the user of the kit.

A kit may comprise a carrier being compartmentalized to receive in close confinement therein one or more container means or series of container means such as test tubes, vials, flasks, bottles, syringes, or the like. A first of said container means or series of container means may contain the monoclonal antibody (or fragment thereof) or PSMA or PSM'. A second container means or series of container means may contain a label or linker-label intermediate capable of binding to the primary antibody (or fragment thereof), PSMA or PSM'.

5.4.3 In Vivo Diagnostic, Prophylactic and Therapeutic Uses

The monoclonal antibodies or fragments thereof of this invention are particularly useful for targeting prostate cancer cells in vivo. They can be used for tumor localization for detection and monitoring as well as for therapy of primary prostate carcinoma and metastases. For these in vivo applications, it is preferable to use purified monoclonal antibodies or purified fragments of the monoclonal antibodies having at least a portion of an antigen binding region, including such as Fv, F(ab')$_2$, Fab fragments (Harlow and Lane, 1988, Antibody Cold Spring Harbor), single chain antibodies (U.S. Pat. No. 4,946,778), chimeric or humanized antibodies (Morrison et al., 1984, Proc. Natl. Acad. Sci. USA 81:6851; Newuberger et al., 1984 Nature 81:6851), CDR, and the like. Purification of the antibodies or fragments can be accomplished by a variety of methods known to those of skill including, precipitation by ammonium sulfate or sodium sulfate followed by dialysis against saline, ion exchange chromatography, affinity or immunoaffinity chromatography as well as gel filtration, zone electrophoresis, etc. (see Goding in, Monoclonal Antibodies: Principles and Practice, 2d ed., pp 104-126, Orlando, Fla., Academic Press).

For use in in vivo detection and/or monitoring of prostate carcinoma, the purified monoclonal antibodies can be covalently attached, either directly or via a linker, to a compound which serves as a reporter group to permit imaging of specific tissues or organs following administration and localization of the conjugates or complexes. A variety of different types of substances can serve as the reporter group, including such as radiopaque dyes, radioactive metal and non-metal isotopes, fluorogenic compounds, fluorescent compounds, positron emitting isotopes, non-paramagnetic metals, etc.

For use in in vivo therapy of prostate carcinoma, the purified monoclonal antibodies can be used alone or covalently attached, either directly or via a linker, to a compound which kills and/or inhibits proliferation of the malignant cells or tissues following administration and localization of the conjugates. When the antibody is used by itself, it may mediate tumor destruction by complement fixation or antibody-dependent cellular cytotoxicity. Alternatively, the antibody may be administered in combination with a chemotherapeutic drug to result synergistic therapeutic effects (Baslya and Mendelsohn, 1994 Breast Cancer Res. and Treatment 29:127-138). A variety of different types of substances can be directly conjugated to the antibody for therapeutic uses, including radioactive metal and non-metal isotopes, chemotherapeutic drugs, toxins, etc. (Vitetta and Uhr, 1985, Annu. Rev. Immunol. 3:197).

According to an alternative embodiment, for in vivo therapy of prostate carcinoma the monoclonal antibodies of the present invention can be modified to be in the form of a bifunctional or bispecific antibody, i.e., an antibody having an antigen-binding region specific for the extracellular domain of prostate specific membrane antigen and an antigen-binding region specific for an effector cell which has tumorcidal or tumor inhibitory activity. The two antigen binding regions of the bispecific antibody are either chemically linked or can be expressed by a cell genetically engineered to produce the bispecific antibody. (See generally, Fanger et al., 1995 Drug News & Perspec. 8(3):133-137). Suitable effector cells having tumorcidal activity include but are not limited to cytotoxic T-cells (primarily CD8$^+$ cells), natural killer cells, etc. An effective amount of a bispecific antibody according to the invention is administered to a prostate cancer patient and the bispecific antibody kills and/or inhibits proliferation of the malignant cells after localization at sites of primary or metastatic tumors bearing PSMA.

Methods for preparation of antibody conjugates of the antibodies (or fragments thereof) of the invention useful for detection, monitoring and/or therapy are described in U.S. Pat. Nos. 4,671,958; 4,741,900 and 4,867,973.

Antibodies and antigen-binding antibody fragments may also be conjugated to a heterologous protein or peptide by chemical conjugation or recombinant DNA technology. The resultant chimeric protein possesses the antigen-binding specificity of the antibody and the function of the heterologous protein. For example, a polynucleotide encoding the antigen binding region of an antibody specific for the extracellular domain of PSMA can be genetically fused to a coding sequence for the zeta chain of the T cell receptor. After expressing this construct in T cells, the T cells are expanded ex vivo and infused into a prostate cancer patient. T cells expressing this chimeric protein are specifically directed to tumors that express PSMA as a result of the antibody binding specificity and cause tumor cell killing. Alternatively, an antibody is fused to a protein which induces migration of leukocytes or has an affinity to attract other compounds to a tumor site. A specific protein of this type is streptavidin. The binding of a streptavidin-conjugated antibody to a tumor cell can be followed by the addition of a biotinylated drug, toxin or radioisotope to cause tumor specific killing.

Kits for use with such in vivo tumor localization and therapy methods containing the monoclonal antibodies (or fragments thereof) conjugated to any of the above types of substances can be prepared. The components of the kits can be packaged either in aqueous medium or in lyophilized form. When the monoclonal antibodies (or fragments thereof) are used in the kits in the form of conjugates in which a label or a therapeutic moiety is attached, such as a radioactive metal ion or a therapeutic drug moiety, the components of such conjugates can be supplied either in fully conjugated form, in the form of intermediates or as separate moieties to be conjugated by the user of the kit.

6. EXAMPLE

Production of a Monoclonal Antibody Against a PSMA PEPTIDE

6.1. Materials and Methods

6.1.1 Preparation of Immunizing Peptide

PSMA peptide #716-723 (NH$_2$-ESKVDPSK-) (SEQ ID NO: 1) was coupled to keyhole limpet hemocyanin (KLH) as a carrier using the EDC method of Pierce (Rockford, Ill.). The peptide KLH complex was emulsified in incomplete Freund's adjuvant (Sigma, St. Louis, Mo.) containing 1 mg/ml muramyl-dipeptide (MDP, Pierce, Rockford, Ill.) at a final concentration of 250 μg/ml. The emulsified antigen preparation was stored at 4° C.

6.1.2 Immunization

BALB/c female mice were immunized subcutaneously with 0.1 ml of the emulsified peptide carrier-complex every fourteen days for a period of six weeks. The mice were bled and their sera were tested in a peptide-specific radioimmune assay (RIA) for the presence of anti-peptide antibodies. Mice that tested positive for anti-peptide antibodies with a titer of 1:1,000 or greater were used as donors in a fusion protocol. Three days prior to fusion, the mice were immunized intraperitoneally with 50 μg of peptide-KLH complex dissolved in saline.

6.1.3 Cell Fusion

Three days following the final boost with the same peptide-KLH complex, the spleen of a BALB/c mouse was aseptically removed and a single cell suspension was prepared. The red blood cells were lysed by osmotic shock and the remaining lymphocytes were suspended in RPMI-1640 medium. The splenocytes were mixed with P3X63Ag8U.1 (X63) myeloma cells (CRL 1597 from ATCC, Rockville, Md.) at a ratio of 10:1 (100×10$^6$ splenocytes: 10×10$^6$ X63 myeloma cells). Fusion of the splenocytes to X63 cells was performed by the method of Galfre and Milstein (1981, Methods in Enzymology, Vol. 73, Immunochemical Techniques, Part B). Hybridoma cells were selected by the inclusion of aminopterin in the cell culture medium (RPMI-1640-20% fetal calf serum).

6.1.4 Screening of Primary Hybridomas

Fifty microliters (μl) of cell culture supernatant were removed from individual hybridoma cultures and tested in a peptide-specific RIA for the presence of peptide-specific antibodies. Briefly, the supernatants were added to wells of a 96-well Pro-Bind plate (Falcon) that had previously been coated with peptide coupled to bovine serum albumin (BSA) at 50 μg/ml. Following an overnight incubation at 4° C., the plates were washed four times with PBS-0.1% BSA. Fifty microliters of a 1:500 dilution of rabbit anti.-mouse IgM and IgG (ICN) were added to each well and the plates were incubated for 1 hour at room temperature. The plates were washed four times as above and 50 μl of $^{125}$I-Protein A was added to each well. The plates were incubated for 1 hour at room temperature and washed 4 times as above. The plates were exposed to autorad film (Kodak, X-OMAT) overnight and developed. Positive wells were selected and the cells were expanded in cell culture medium for further testing.

6.1.5 Western Blot Screening

Supernatants from the positive and expanded wells were tested in a Western blot assay for anti-PSMA antibodies. Lysates from the LNCaP tumor cell line (CRL 1740 from ATCC, Rockville, Md.), a prostate tumor that expresses PSMA, were run on a SDS-polyacrylamide gel for 90 minutes at 175 volts. The electrophoresed proteins were electroblotted to an Immobilon-P™ membrane and the membrane was blocked by an overnight incubation with 5% BLOTTO in Tris-buffered saline. The membrane was placed in a Bio-Rad multi-screen apparatus (Bio-Rad) and approximately 650 μl of hybridoma supernatant were pipetted into individual lanes. The membrane was incubated for 90 minutes at room temperature and the blot was washed 5 times with Tris-buffered saline-0.5% Tween-20 (TBS-T). The washed blot was incubated with a 1:5,000 dilution of peroxidase-labelled goat anti-mouse IgG (Kirkegaard and Perry Laboratories, Gaithersburg, Md.) for 1 hour at room temperature. The blot was washed 5 times as above and incubated for 1 minute with 2 ml of LumiGLO™ chemiluminescent substrate (KPL, Gaithersburg, Md.). The blot was exposed to autorad film and developed. Positive hybridoma wells (anti-PSMA reactivity) were identified and selected for further development.

6.1.6 Limiting Dilution Cloning

The positive primary hybridoma wells identified by their reactivity to PSMA in the Western blot assay described above were cloned by limiting dilution. The cells were adjusted to 1 cell/ml in complete cell culture medium containing syngeneic thymocytes as feeder cell population. The cell suspension was dispensed in 200 μl aliquots into the wells of a 96-well plate. Following 7-10 days of culture, colonies of cells were visible. Wells containing single colonies were picked and the cells were expanded in 24-well plates (1.5 ml cultures). Supernatants from the clonal cells were harvested and tested for anti-PSMA antibodies in the Western blot assay described above. Positive clones were expanded and frozen in liquid nitrogen.

6.1.7 Generation of Ascites Fluid and Antibody Purification

BALB/c mice were primed with 0.4 ml pristane intraperitoneally 7-10 days prior to the injection of 10×10$^6$ hybridoma cells. The ascites fluid containing monoclonal antibody was drained at periodic intervals and stored at 4° C. The monoclonal antibody was purified from ascites fluid using the ImmunoPure™ IgM Purification Kit from Pierce (Rockford, Ill.).

6.1.8 Immunoprecipitation of PSMA

Approximately $10\times10^6$ LNCaP tumor cells were incubated with 1 ml of NP-40 lysis buffer (150 MM NaCl, 1% NP-40, 50 mM Tris) for 30 minutes at 4° C. The lysate was centrifuged at 12,000 rpm and the resultant supernatant was precleared by incubating with 50 μl of normal mouse serum for 30 minutes followed by the addition of 60 μl of a 20% suspension of anti-mouse IgM agarose beads. Following incubation for 1 hour at 4° C., the preparation was centrifuged to remove the beads and the resultant supernatant was reacted with 3F5.4G6 monoclonal antibody. Varying amounts of 3F5.4G6 monoclonal antibody (2.5, 5, and 10 μg) was added to three replicate lysates and incubated for 1 hour at 4° C. One-hundred microliters of a 10% suspension of anti-mouse IgM agarose beads (Sigma) were added and the lysates were incubated for an additional hour at 4° C. The lysates were centrifuged at 12,000 rpm and the agarose beads were washed three times with NP-40 lysis buffer. Thirty microliters of electrophoresis sample buffer were added to the beads and they were heated for ten minutes at 95° C. The beads were centrifuged briefly at 12,000 rpm and the sample buffer was loaded onto an SDS-polyacrylamide gel. Following electrophoresis, the samples were electroblotted as described above and a western blot was performed using the PSMA-specific monoclonal antibody 7E11-C5 as the reporting antibody.

6.1.9 Flow Cytometric Anaylsis

Cells were first rinsed with phosphate buffered saline (PBS). Versene (0.2 g EDTA. 4Na/L) solution (2m1 for a 75 cm flask) was added. Most of the Versene solution were removed by aspiration prior to incubation at room temperature for 5 minutes. PBS was added and the cells were dislodged by pipetting. The cells were washed twice with PBS and counted. Five hundred thousand to one million cells were incubated on ice with 50 μl primary antibody for 30 minutes, followed by two washes with PBS. The cells were subsequently incubated on ice with 50 μl FITC-labelled secondary antibody (goat-antimouse IgG for 7E11-C5 or goat-antimouse IgM for 4G6) for 30 minutes. Excess secondary antibody was washed off the cells with PBS. Fluorescence was analyzed using a flow cytometer (FACScan, Becton Dickinson, San Jose, Calif.). Cell debris were excluded from the cell populations which were analyzed based on their forward and side scatter profiles.

6.1.10 Serum Assays by Western Blot

Serum samples were diluted 1:7 in lysis buffer (1% Triton X-100, 50 mM HEPES, 10% glycerol, 15 mM $MgC1_2$, 1 mM AEBSF, 1 mM EGTA). LNCaP lysate was diluted 1:35 in lysis buffer. The diluted samples were then combined at a ratio of 2:3 with sample buffer (SDS reducing buffer). Samples (20 μ) were run on 8.5% SDS-PAGE (final protein concentration of 93 mg per sample, as determined using the Bio-Rad Protein Assay), and the separated proteins were blotted on PVDF membrane for one hour at 90 volts. Membranes were then blocked overnight in 5% milk-TBS. The next day, the membranes were probed with 3 μg/ml 7E11-C5 antibody in TBS-T for one hour, washed 5 times for five minutes in TBS-T, and probed with 167 ng/ml sheep anti-mouse horse radish peroxidase-labeled secondary antibody in TBS-T for 30 minutes. Again, the membranes were washed 5 times for five minutes each in TBS-T and the membranes developed using. Chemiluminescent Substrate Kit (Kirkegaard & Perry Laboratories, Inc., Gaithersburg, Md.) (Rochon et al., 1994, The Prostate 25:219-223).

Blots were visualized by exposing X-ray film, revealing a protein band of approximately 120 kD. The blot image was scanned with a Microtek ScanMaker IIHR scanner and band intensities measured by "analysis performed on a Macintosh Quadra 605 computer using the public domain NIH image program (written by Wayne Rasband at the U.S. National Institutes of Health and available from the Internet by anonymous ftp from zippy.nimh.nih.gov or on floppy disk from NTIS, S285 Port Royal Rd., Springfield, Va. 22161, part number PB93-504868)". All patient samples were assessed against a healthy normal donor sample, and a prostate cancer patient sample with a high PSMA, from the same Western blot as standard controls.

6.1.11 Detection of PSM' Enzymatic Activity

One hundred ml of human semen were collected from paid donors under the WHO guidelines for fertility testing. The cellular material was pelleted by centrifugation at 10,000 rpm for 30 minutes and the supernatant carefully removed and dialyzed overnight against two changes of 20 mM Tris buffer, pH 7.6. The dialysate was centrifuged again at 10,000 rpm and loaded onto a DEAF sephacryl column which was previously washed with 20 mM Tris buffer, pH 7.6. The loaded column was then washed again with 500 ml of the same buffer and the proteins separated by applying a 20 mM to 200 MM Tris buffer gradient at pH 7.6. Fractions of 5 ml were collected. PSMA presence in each fraction was determined by Western dot blot using the monoclonal antibody 7E11-C5. Fractions containing 7E11-C5 reactive protein bands were pooled and precipitated using 70% ammonium sulfate. The precipitated proteins were pelleted by centrifugation at 10,000 rpm for 30 minutes and then resuspended in 1 liter of 200 mM Tris buffer, pH 7.6. The solubilized proteins were then dialyzed overnight against two changes of 20 mm Trist buffer, pH.7.6. The dialyzed material was then loaded onto a prewashed Sephacryl column and the proteins eluted, three ml fractions were collected. A Western dot blot was performed on the eluted protein using the monoclonal antibody 3F5.4G6. Fractions 88-96 were positive and each of these fractions was tested for purity by SDS polyacrylamide gel electrophoresis.

6.2. Results

In order to generate monoclonal antibodies to the extracellular domain of PSMA, several regions of the protein were analyzed with respect to their relative hydrophilicity based on the Hopp and Woods method (1983, Mol. Immunol. 20:483-489).

Table 1, below, illustrates the relative hydrophilicity of several peptides examined. In particular, a peptide having the sequence of ESKVDPSK (Glu-Ser-Lys-Val Asp-Pro-Ser-Lys) (SEQ ID NO: 1) was synthesized corresponding to amino acid residue numbers 716-723 of SEQ ID NO:2 in the C-terminal region of PSMA. Additionally, other portions of the extracellular domain as shown in Table 1 or the entire extracellular domain itself could be used to produce antibodies to the extracellular domain. In contrast, two amino acid peptides corresponding to residue #44-58 and residue #196-213 of SEQ ID NO:2 induced anti-peptide antibody responses that did not bind to native PSMA.

TABLE 1

Relative hydrophilicity of PSMA peptides

| PEPTIDE (amino acid # of SEQ ID NO: 2) | RELATIVE HYDROPHILICITY |
|---|---|
| 63-69 | 1.41 |
| 183-191 | 1.24 |
| 404-414 | 1.45 |

TABLE 1-continued

Relative hydrophilicity of PSMA peptides

| PEPTIDE (amino acid # of SEQ ID NO: 2) | RELATIVE HYDROPHILICITY |
|---|---|
| 479-486 | 1.5 |
| 716-723 | 1.39 |

Prior to immunization, the peptide ESKVDPSK (SEQ ID: NO 1) was first conjugated to KLH as a carrier. Mice were then immunized and boosted with the same conjugated material at weekly intervals. Spleens of animals with a detectable anti-peptide serum titer were isolated and fused with myeloma cells.

Initial screenings were performed by binding assays using peptide-bound-BSA as antigen. Fifty µl of cell culture supernatant were removed from individual hybridoma cultures and tested in a peptide-specific radioimmunoassay for the presence of peptide-specific antibodies. Briefly, the supernatants were added to wells of a 96 well Pro-Bind plate that had previously been coated with peptide coupled to bovine serum albumin (BSA). Following an overnight incubation at 4° C., the plates were washed with PBS. Fifty µl of a 1:500 dilution of rabbit anti-mouse IgM and IgG were added to each well and the plates incubated for 1 hr at room temperature. The plates were then washed 4x and 50 µl of $^{125}$I-Protein A was added to each well. The plates were incubated for 1 hr at room temperature and washed 4x as above. The plates were exposed to autorad film overnight and developed. Positive wells were selected and the cells were expanded in cell culture medium for further testing. Among the positive wells identified, one hybridoma designated 3F5 was further tested in a western blot assay and its secreted antibody was shown to react with PSMA contained in LNCaP lysates. LNCaP cells were cultured as described by Horoszewicz et al. (1983, Cancer Res. 43:1809-1818), and the lysates prepared as described by Rochon et al. (1994, Prostate 25: 219-223). The 3F5 hybridoma cells were cloned by limiting dilution, expanded in numbers and retested in a Western blot assay. A subclone of the antibody referred to as 3F5.4G6 reacted with a protein of 120 kDa molecular weight in the LNCaP lysates (FIG. 2). This antibody was isotyped as an IgM. ISOStrip obtained from Boehringer Mannheim for isotyping mouse monoclonal antibodies was used for determining the isotype of 3F5.4G6. The monoclonal antibody was diluted 1:100 in PBS and the diluted sample (150 µl) added to a development tube supplied with the kit and incubated for 30 seconds at room temperature and then agitated briefly. The isotype strip was then inserted into the tube and developed for 5 minutes. A blue band appeared in either the lambda or kappa section of the strip as well as in one of the class or subclass sections. Monoclonal antibody 3F5.4G6 was identified as an IgM isotype.

Monoclonal antibody 3F5.4G6 was further tested against sera taken from stage D2 prostate cancer patients in progression, using monoclonal antibody 7E11-C5 as a control (FIG. 3). Both antibodies identified a band of about 120 kDa molecular weight (FIG. 3). An additional Western blot assay of LNCaP cells using the 3F5.4G6 monoclonal antibody was performed using a secondary antibody specific for IgM (FIG. 4). While monoclonal antibody 7E11-C5 recognized a single band of about 120 kDa, i.e., PSMA, 3F5.4G6 recognized a similar molecular weight band as well as a band of about 105-110 kDa. This band corresponds to the predicted protein form of PSM', and demonstrates the utility of an antibody that specifically recognizes the extracellular domain of both PSMA and PSM'.

The reactivity of 7E11-C5 with a protein of 120 kDa in the sera of prostate cancer patients was antibody-specific, and not due to the non-specific reactivity of the secondary antibody with serum proteins in general. In a Western blot assay, Immobilon P paper containing separated proteins derived from serum samples was reacted with either 7E11-C5 monoclonal antibody plus secondary antibody coupled to HRP or to secondary antibody coupled to HRP only. The film was exposed for 1 min or overexposed for 45 min in order to demonstrate the non-reactivity of the secondary antibody with any protein of 120 kDa in sera. The same secondary antibody was also used with 3F5.4G6 to detect the same antigen. Therefore, the 3F5.4G6 monoclonal antibody was specific for PSMA and PSM'.

FIG. 5 confirms that the protein identified by 7E11-C5 was also recognized by monoclonal antibody 3F5.4G6. In addition, monoclonal antibody 3F5.4G6 also recognized a protein of 105-110 kDa not detected by monoclonal antibody 7E11-C5. This faster migrating protein corresponded to PSM'. When the lysate was first precipitated with 7E11-C5, and the remaining proteins probed with 7E11-C5, the antibody did not detect any protein (Lane 4). In contrast, when the 7E11-C5 pre-treated lysate was probed with 3F5.4G6, it detected a protein of about 110 kDa. FIG. 6 shows that the 120 kDa protein, i.e. PSMA, immunoprecipitated by 3F5.4G6 was also recognized by 7E11-C5.

FIG. 7A and B demonstrates that monoclonal antibody 3F5.4G6 recognized live LNCaP cells by FAGS analysis, confirming that 3F5.4G6 recognized the extracellular domain of PSMA. Such an antibody recognizing the extracellular domain of PSMA is particularly useful as a diagnostic and/or therapeutic tool in prostate cancer.

Human seminal fluid was reacted with a PSMA-specific antibody and assayed for enzymatic activity. FIG. 8 illustrates that the protein recognized by monoclonal antibody 3F5.4G6 in Lane 2 is of approximate molecular weight 90 kDa. While PSM' was shown to have a molecular weight of 105-110 kDa in LNCaP lysates, the 90 kDa protein in seminal fluids was likely to be a non-glycosylated or partially glycosylated product of PSM'. Since PSM' contains several glycosylation sites, this lower molecular weight was the result, of activities by glycosidases in the seminal fluid. That PSMA was not present in this purified preparation is illustrated by the fact that 3F5.4G6 recognized a protein of molecular weight 120 kDa (Lane 1) present in a lysate of LNCaP cells which is PSMA, but did not recognize a protein of this molecular weight in Lane 2. In addition, antibody 7E11-C5 did not recognize the 90 KDa band in seminal fluids.

This purified preparation of PSM' recognized by monoclonal antibody 3F5.4G6 was then assayed for NAALADase activity. The high speed supernatant prepared from a LNCaP lysate was used as a positive control. The protein reacting positively with the 3F5.4G6 monoclonal antibody and being consistent with it being PSM', contained inherent NAALA-Dase activity of 16.9 nmol/min./mg protein using the assay described in Robinson et al. (1987, J. Biol. Chem. 262:14498-14506).

7. EXAMPLE

Production of Monoclonal Antibodies Against a PSMA-Containing Tumor Cell Membrane Preparation

7.1. Materials and Methods

7.1.1 Immunization

LNCaP prostatic carcinoma cells were obtained from the American Type Culture Collection (ATCC), Rockville, Md. LNCaP membranes were prepared from two 150 mm plates by removing cells in a versene solution followed by centrifugation to pellet the cells. Distilled water was added to the cell pellet and the cells were homogenized using a dounce homogenizer. The homogenized suspension was centrifuged at 30,000×g and the pelleted membrane fraction used for immunization.

Adult female BALB/c mice were immunized intraperitoneally four times (2-3 week intervals) with a LNCaP membrane preparation emulsified in complete Freund's Adjuvant. Five days prior to cell fusion, the mice were boosted with 50 µg of immunoaffinity purified PSMA in PBS. Cell fusion was performed as described in Section 6.1.3 supra.

7.1.2 Screening of Primary Hybridomas

A solid-phase enzyme-linked immunoadsorbant assay (ELISA)-based assay was employed for the detection of PSMA-specific antibodies. Immunoaffinity purified PSMA, Baculovirus-expressed full-length PSMA, or bacterially-expressed fusion proteins containing PSMA fragments were coated onto Maxi-Sorp (Nunc Immuno, Rochester, N.Y.) 96-well plates with an overnight incubation at 4° C. The plates were washed with PBS-0.2% Tween-20 and the remaining sites were blocked with a 5% solution of BSA for one hour at room temperature. Fifty microliters (µl) of supernatant from the hybridoma cultures were added to the PSMA-coated wells and the plates were incubated for two hours at room temperature. The plates were washed as above and 50 µl of 1:600 dilution of rabbit-anti-mouse IgG and rabbit-anti-mouse IgM (ICN, Costa Mesa, Calif.) were added to each well. Following a one hour incubation at room temperature, the plates were washed as above and 50 µl of a 1:400 dilution of HRP-conjugated Protein-A (Sigma, St. Louis, Mo.) were added to each well. Following a one hour incubation at room temperature, the plates were washed as above and 100 µl ABTS (150 mg 2,2'-azino-bis (3-ethylbenzthiazoline-6-sulfonic acid in 500 ml of 0.1 M citric acid, pH 4.35)/$H_2O_2$ (10 µl 30%–$H_2O_2$ per 10 ml of ASTS solution)chromogen/substrate solution were added to each well. The plates were read in a microplate reader and the OD405 was measured. The hybridoma cells producing supernatants with OD values 0.05 above background were cloned by limiting dilution and subjected to additional analysis.

For solid-phase capture of PSMA, the aforementioned assay was modified as follows: Fifty microliters of a 40 µg/ml solution of 7E11-C5 anti-PSMA monoclonal antibody in 0.1 M $NaHCO_2$, pH 8.2 binding buffer were added to wells of a Maxi-Sorp plate and allowed to adhere overnight at 4° C. The plates were washed and blocked as above. Fifty microliters of serially-diluted immunoaffinity-purified PSMA were added to the 7E11-C5-coated wells and the plates were incubated for two hours at room temperature. Following extensive washing, 50 µl of undiluted tissue culture supernatant from either 3D7-1.1 or 4E10-1.14 hybridoma clones were added to the wells and the plates were incubated for 90 minutes at room temperature. After washing as above, the wells were probed with 50 µl of a 1:1.000 dilution of peroxidase-conjugated goat anti-mouse IgM and incubated for one hour at room temperature. Following extensive washing, 100 µl of ARTS/$H_2O_2$ were added to each well and the plates were read in a microplate reader as described above.

7.1.3 Immunoaffini'y Purification of PSMA

Sixteen milliliters of packed LNCaP cells were homogenized in 5 volumes of 25 mM Tris-HCL, pH 7.4, 150 mM NaCl, 1% NP-40 (Sigma, St. Louis, Mo.) by two strokes of a Potter-Elvehjem homogenizer followed by stirring overnight at 4° C. The extract was centrifuged at 100,000×g for 1 hour and the pellet re-extracted as before. The combined supernatants were mixed in the cold overnight with 7E11-C5-Immunobeads (Pierce, Rockford, Ill.) (3-5 ml resin bed volume). The beads were centrifuged, washed extensively with homogenization buffer and poured into a column. The beads were washed again with additional homogenization buffer containing 1% NP-40 followed by an additional wash with buffer containing 1% Triton X-10OR (Aldrich, Milwaukee, Wis.). The washed beads were eluted with 1.00 mM glycine buffer, pH 2.5, 150 mM NaCl, 1% Triton X-10OR in 2 ml fractions. Protein elution was monitored at OD280.

Fractions containing protein were analyzed by SDS-PAGE gels using silver staining and Western blotting. In typical preparations, the 120 kDa protein band corresponding to 7E11-C5 reactivity in a Western blot was 60-80% pure. An approximate yield from 16 ml of packed cells was 1 milligram of PSMA protein. The detergent in the PSMA preparation was removed by passing the solution over an Extractigel column (Pierce). The protein was lyophilized and dialyzed extensively with PBS prior to use in immunization or hybridoma screening.

7.1.4 Flow Cytometric Analysis

The ability of monoclonal antibodies to recognize external or extracellular epitopes of PSMA was assessed by flow cytometry. LNCaP (PSMA-expressing) and PC-3 cells (PSMA-non-expressing) were freshly harvested from tissue culture flasks and a single cell suspension prepared. Approximately one million cells were resuspended in one ml of undiluted tissue culture supernatant from either 3D7-1.1 or 4E10-1.14 hybridoma clones and incubated on ice for two, hours. The cells were washed two times with PBS-0.1% BSA, 0.01% Na azide, resuspended in 100 µl of a 1:100 dilution of FITC-conjugated rabbit-anti-mouse IgM (Jackson ImmunoResearch, WestGrove, Pa.), and incubated on ice for an additional 30 minutes. The cells were washed twice as above, resuspended in 500 µl of wash buffer, and analyzed for fluorescent staining by FACSCalibur (Becton-Dickinson, San Jose, Calif.) with CellQuest acquisition software.

7.1.5 Western Slot Analysis

Tissue culture supernatants from the 3D7-1.1 and 4E10-1.14 hybridoma clones were tested in a Western blot assay for PSMA reactivity. Western blot analysis was performed following the protocol of Pelletier and Boynton (1994, J. Cell. Physiol. 158:427-434). Briefly, lysates from LNCaP and PC-3 cells, immunoaffinity-purified PSMA, or Baculovirus-expressed full-length PSMA were electrophoresed on an 8.5% SDS-PAGE gel, and the separated proteins were electroblotted onto a PVDF membrane for one hour at 90 volts. The membranes were blocked overnight in 5% BLOTTO and incubated for 90 minutes with 20 ml undiluted tissue culture supernatant from the appropriate clone. The supernatant was removed, the blots were washed five times with TBS-0.5% Tween-20 (TBS-T), and probed with a 1:5,000 dilution of peroxidase-conjugated goat-anti-mouse IgM secondary antibody (Jackson) for one hour at room temperature. The membrane was washed five times with TBS-T, developed using the Chemiluminescent Substrate Kit (KPL, Gaithersburg, Md.), and visualized by exposing X-ray film (Kodak).

7.1.6 Preparation of Recombinant PSMA by Baculovirus Expression System

An insert containing the full length coding sequence of PSMA (Israeli et al., 1993, Cancer Res. 53:227 230) was cloned from a Lambda pDR2 human library (Clontech, Palo Alto, Calif.) using probes specific for the gene sequence. The insert was excised from this vector by SmaI and SspI digestion and cloned into the transfer vector pAcHLT-C (Pharmingen, San Diego, Calif.) according to manufacturer's instructions. Co-transfection of the transfer vector with Bac-PAK6 linearized viral DNA (Clontech) yielded virus encoding full length PSMA protein containing a poly-histidine tail at the N-terminal of the protein to be used for protein isolation by binding to an Ni-NTA-column. PSMA protein was produced by isolating plaque-purified recombinant baculovirus particles, amplifying and infecting Sf9 cells at a multiplicity of infection of about 1:2 in the presence of SFM II medium (Gibco-BRI, Gaithersburg, Md.) supplemented with 5% FES (Hyclone, Logan, Utah). Following a 48 hr incubation, infected cells were harvested and lysed in 1% CHAPS, and recovered via Ni-NTA-Agarose (Quiagen, Chatsworth, Calif.) with imidazole elution according to manufacturer's instructions. The final product was dialyzed extensively against PBS.

7.2. Results

Monoclonal antibodies were generated against PSMA-containing prostatic carcinoma membranes. Two hybridoma clones, 3D7-1.1 and 4E10-1.14, were selected by a solid-phase immunoassay using immunoaffinity-purified native PSMA from LNCaP cells and bacterially-expressed fragments of PSMA corresponding to amino acid regions 1-173, 134-437, and 438-750 of SEQ ID NO:2. Supernatants from 3D7-1.1 and 4E10-1.14 hybridoma clones demonstrated comparable binding to native PSMA as compared to antibody 7E11-C5 (FIG. 9). Background non-specific binding to BSA was essentially comparable for all three antibody preparations.

When epitope binding specificity was tested, 7E11-C5 monoclonal antibody bound to the amino acid fragment 1-173 of SEQ ID NO:2 which contains the N-terminal, intracellular domain of PSMA. Although 3D7-1.1 and 4E10-1.14 displayed modest binding to this fragment, these two monoclonal antibodies demonstrated the strongest binding to the amino acid fragment 134-437 of PSMA, which is part of the extracellular domain of PSMA of SEQ ID NO:2 (FIG. 9). Since this fragment is a part of PSM', these antibodies also react with PSM'.

Supernatant from the 3D7-1.1 hybridoma clone was further tested in a Western blot assay against lysates from LNCaP and PC-3 cells, and immunoaffinity-purified PSMA. FIG. 10 shows that 3D7-1.1 reacts with a 120 kDa band present in LNCaP cells (Lane 1) but not in PC-3 cells (Lane 2). Both Lanes 1 and 2 display reactivity that was most likely due to non-specific binding of the secondary antibody reagent. Lane 3 containing immunoaffinity purified PSMA shows a major band at 120 kDa when probed with 3D7-1.1 monoclonal antibody. Similar Western blot data were also obtained with supernatant from the 4E10-1.14 clone although the non-specific background of the blot was much greater than with 3D7-1.1. Thus, both 3D7-1.1 and 4E10-1.14 react with a 120 kDa band present in LNCaP cells and with immunoaffinity-purified PSMA.

Full-length Baculovirus-expressed PSMA was electrophoresed on an SDS-PAGE gel and electroblotted to a PVDF membrane. The blot was inserted into a Mini-Protean II Multi-Screen apparatus (Bio-Rad), probed with a variety of antibody preparations, and developed as a western blot. FIG. 11 shows that 3D7-1.1 and 4E10-1.14 monoclonal antibodies reacted with a protein band that corresponded to the same band bound by 7E11-C5 monoclonal antibody.

LNCaP cells and PC-3 cells were stained with supernatants from 3D7-1.1 and 4E10-1.14 hybridoma-clones and analyzed by flow cytometry. Both antibodies stained live, non-fixed LNCaP cells but did not stain PC-3 cells (FIG. 12A-D). These results confirm that these two antibodies react with epitopes in the extracellular domain of the PSMA molecule. Furthermore, the distinct shift in LNCaP staining observed with 4E10-1.14 monoclonal antibody compared to the shoulder seen with 3D7-1.1 suggests that these two antibodies recognize different epitopes in this particular region of the PSMA molecule.

A two-site capture ELISA for PSMA was developed utilizing the 7E11-C5 monoclonal antibody as a PSMA-capture reagent and 3D7-1.1 and 4E10-1.14 monoclonal antibodies as reporting or detection antibodies. Since these antibodies recognize different epitopes on the PSMA molecule (7E11-C5 reactive with the N-terminal 6 amino acids; 3D7-1.1 and 4E10-1.14 reactive with a sequence in the 134-475 amino acid region of SEQ ID NO:2, they pair effectively in the two-site capture assay. Using serially diluted immunoaffinity purified PSMA as a test antigen, supernatants from both 3D7-1.1 and 4E10-1.14 were able to detect PSMA following capture on 7E11-C5-coated 96-well plates (FIG. 13). Additionally, purified PSMA from LNCaP cells and seminal fluid was tested as well as a crude preparation of baculovirus-expressed full-length PSMA (FIG. 14). Significant $OD_{405}$ readings were observed for the PSMA control antigen, seminal fluid, and the baculovirus PSMA preparation. When purified PSMA was diluted in normal female human serum and the samples were assayed using the two-site capture assay, the same antibodies also detected PSMA (FIG. 15). Hence, the two-site capture assay developed with monoclonal antibodies directed to different portions of PSMA detected PSMA from a variety of sources in an antigen-specific manner.

An alternative two-site capture ELISA for PSMA was developed using -3D7-1.1 monoclonal antibody as a PSMA capture reagent and 7E11-C5 monoclonal antibody as a reporter or detection antibody. Serially diluted immunoaffinity purified PSMA was used as test antigen, captured on 3D7-1.1 coated plates and detected using biotinylated 7E11-C5 monoclonal antibody. Results are shown in FIG. 16. FIG. 16 demonstrates that monoclonal antibodies such as 3D7-1.1 or 4E10-1.14 which bind specifically to the extracellular domain of PSMA are useful in a two-site capture ELISA for PSMA.

The utility of 3D7-1.1 for capture of PSMA indicates that another alternative immunoassay relying exclusively on the extracellular domain of the PSMA protein will be useful. Such an assay utilizing two extracellular domain-specific antibodies for capture and detection would be able to detect PSM' because of the location in the protein of its epitope. Thus, any assay utilizing 7E11-C5 for either capture or detection would specifically exclude PSM'. An example of a PSM' specific assay would include capture of PSMA and PSM' by an antibody such as 3D7-1.1 or any one of the monoclonal antibodies specific for the extracellular domain of PSMA in parallel tests. Subsequent detection using both 4E10-1.14 for total PSMA and PSM', and 7E11-C5 for only PSMA would yield the amount of PSM' by simple subtraction. From this data a ratio of PSM' to PSMA is derived which will have diagnostic relevance in view of the reference by Su et al., Cancer Res., 55:1441-1443 (1995).

Su shows that the transcript encoding PSMA is preferentially detected in prostate cancer patients (compared to normal males) although Su presents no demonstration that the PSMA transcript is in fact translated into protein in these patients. Additionally, Su shows that the transcript encoding PSM' is preferentially detected in normal males (compared to prostate cancer patients), although Su never detected any PSM' protein. The present inventors, in this application, demonstrate that the PSMA protein is enhanced in body tissues and/or fluids of prostate cancer patients (compared to normal males) and that the,PSM' protein is enhanced in body tissues and/or fluids of normal males (compared to prostate cancer patients). Thus, according to the present invention, the ratio of PSM' to PSMA will have diagnostic and/or prognostic utility for clinical assessment of prostate cancer patients.

A fragment of PSMA corresponding to amino acids 34 to 750 of full length PSMA of SEQ ID NO:2 was expressed in a baculovirus expression system as a 1.9 kb insert in a baculovirus expression system. The baculovirus expressed PSMA fragment is very similar to PSM' (which corresponds to residues 58-750 of full length PSMA of SEQ ID NO:2) except that an additional 76 amino acids of the extracellular domain of PSMA are missing from the N-terminal of the fragment. Western blot analysis of various baculovirus expressed semi-purified PSMA fragment and LNCaP cell lysate were developed with monoclonal antibody 4E10-1.14 as probe. Results are shown in FIG. 17.

Western blot analysis of crude lysates of SF9 cells infected with baculovirus containing either an irrelevant insert or the 1.9 kb insert encoding the PSMA fragment, i.e. amino acids 134-750 of full length PSMA of SEQ ID NO:2, was developed with monoclonal antibody 7E11-C5 as probe. Results are shown in FIG. 18.

FIG. 17 indicates that antibodies such as 4E10-1.14 which are specific for the extracellular domain of PSMA are able also to bind a baculovirus expressed protein product very similar to PSM'. In contrast, FIG. 18 indicates that this is not a property of the 7E11-C5 monoclonal antibody due to its epitope specificity (see the negative reactivity of 7E11-C5 with the baculovirus expressed PSMA fragment in FIG. 18). The baculovirus expressed PSM protein fragment is identical to PSM' (which corresponds to residues 58-750 of full length PSM of SEQ ID NO:2) except that it is missing an additional 76 amino acids from the N-terminal, all of which are in the extracellular domain. Because the epitope specificity of both 3D7-1.1 and 4E10-1.14 map to a region of the extracellular domain contained in both PSM' and the 134-750 amino acid PSMA fragment of SEQ ID NO:2 (see FIG. 9), both antibodies would have the inherent property of binding to native PSM', a property not shared by 7E11-C5.

The 3D7-1.1 monoclonal antibody was used as a probe in a Western blot with LNCaP cell derived PSMA as well as human serum and seminal fluid known also to contain PSMA. The results are shown in FIG. 19.

A band corresponding to PSMA migrating at about 120 Kd is present in all fractions. In addition, a second faster migrating band of molecular weight 90 to 100 Kd was observed in the serum and seminal fluid as revealed by antibody 3D7-1.1. This faster migrating band is not observed in Western blots with serum using the 7E11-C5 antibody (see Holmes et al., 1996, The Prostate, Supple. 7:25-29). This faster migrating 3D7-1.1 reactive protein band is most probably PSM, present in biological fluids.

8. EXAMPLE

Production of Monoclonal Antibodies of IgG Isotype Against PSMA

8.1. Materials and Methods

8.1.1 Immunization

BALB/c and A/J mice were immunized intraperitoneally with LNCaP membrane in complete Freund's adjuvant, followed by one subsequent immunization (2-3 week intervals) with cell membrane in incomplete Freund's adjuvant and three boosts with 50 µg of immunoaffinity purified PSMA in PBS. PSMA was purified according to the method described in Section 7.1.3, supra. Five days after the last boost, cell fusion was performed.

8.1.2 Immunocytochemistry

LNCaP cells were grown on glass slides for immunocytochemistry with either viable or fixed cells. Cells were fixed with 4% paraformaldehyde-PBS for 30 minutes at room temperature, washed with 1% BSA-PBS, quenched for 10 minutes in 50 mM $NH_4Cl$ in PBS, and rinsed in to BSA-PBS. Fixed cells were permeabilized with 0.075% Triton X-100 in 1% BSA-PBS for 2 minutes at room temperature.

Primary antibody as culture supernatant (+0.075% Triton X-100 for fixed cells) was added for 60 minutes at 4° C. for viable cells or at room temperature for fixed cells. After primary antibody treatment, viable cells were fixed in cold methanol for 20 minutes. FITC-labeled goat anti-mouse secondary antibody (1:100 diluted in 1% BSA-PBS+0.075% Triton X-100 for fixed cells) was incubated for 60 minutes and washed extensively with 1% BSA-PBS. Slides were mounted with glycerol and examined by fluorescence microscopy.

8.2. Results

Immunization of animals with membrane-derived and immunoaffinity purified PSMA resulted in increasing serum titers after each injection. Cell fusions were performed using spleen cells from animals having serum titers in excess of 1:100,000 dilution. The hybridomas were screened by solid phase ELISA with full length PSMA and compared to reactivity with bacterially expressed fusion proteins containing portions of the PSMA protein as described in Section 7.1.2, supra, except that a secondary anti-mouse IgG reagent was used to select for antibodies of IgG isotype. In addition, antibody reactivity was evaluated by Western blot analysis, flow cytometric analysis and in a sandwich ELISA using antibody 4E10-1.14 as a capture antibody and a peroxidase-conjugated rabbit-anti-mouse IgG secondary antibody.

Solid phase immunoassays were conducted to determine the approximate location of the binding epitope for each IgG monoclonal antibody obtained. The results are summarized in Table 2, which includes the isotype subclass for each antibody. Among the total of 32 antibodies tested, multiple antibodies were found to bind to each PSMA fragment, and all antibodies bound native PSMA. Two antibodies, 3C2 and 3C4, reacted with both the 1-173 and 134-437 fragments of PSMA of SEQ ID NO:2 suggesting that their epitopes are within the overlapping region of these fragments. Three antibodies 3C6, 4D4 and 1G9 only bound native PSMA suggesting that these antibodies recognize a native protein conformation which is not present in any of the denatured PSMA fragments. Two other antibodies, 3G6 and 3F6, also did not bind to PSMA fragments but they were able to bind to denatured PSMA on Western blots.

TABLE 2

Binding Specificity and Isotype of PSMA-Specific Antibodies to Native PSMA and PSMA Fragments of SEQ ID NO: 2

| Antibody | Native PSMA | 1-173 | 134-437 | 437-750 | Isotype[a] |
|---|---|---|---|---|---|
| 3E11 | + | + | − | − | IgG$_{2b}$ |
| 3F6 | + | − | − | − | IgG$_{2b}$ |
| 3G6 | + | − | − | − | IgG$_{2b}$ |
| 2E4 | + | weak | − | − | IgG$_{2a}$ |
| 3C2 | + | + | + | − | IgG$_{2a}$ |
| 3C4 | + | + | + | − | IgG$_{2a}$ |
| 3C9 | + | − | + | − | IgG$_1$ |
| 2C7 | + | − | + | − | IgG$_1$ |
| 2D4 | + | − | + | − | IgG$_{2b}$ |
| 4C8G8 | + | − | + | − | IgG$_{2b}$ |
| 2C4 | + | − | + | − | IgG$_1$ |
| 4C11 | + | − | + | − | IgG$_1$ |
| 1D11 | + | − | + | − | IgG$_{2b}$ |
| 4E8 | + | − | + | − | IgG$_{2b}$ |
| 2G5 | + | − | + | − | IgG$_{2b}$ |
| 4E6 | + | − | + | − | IgG$_1$ |
| 1F4 | + | − | + | − | IgG$_1$ |
| 1G3 | + | − | − | + | IgG$_{2a}$ |
| 4C8B9 | + | − | − | + | IgG$_{2a}$ |
| 2E3 | + | − | − | + | IgG$_{2a}$ |
| 3D8 | + | − | − | + | IgG$_{2a}$ |
| 4F8 | + | − | − | + | IgG$_{2a}$ |
| 3D2 | + | − | − | + | IgG$_{2a}$ |
| 1G7 | + | − | − | + | IgG$_{2a}$ |
| 3D4 | + | − | − | + | IgG$_{2a}$ |
| 3C6 | + | − | − | − | IgG$_1$ |
| 4D4 | + | − | − | − | IgG$_1$ |
| 1G9 | + | − | − | − | IgG$_1$ |
| 5G10 | + | − | + | − | IgG$_1$ |
| 5E9 | + | − | + | − | IgG$_1$ |
| 4D8 | + | + | − | − | IgG$_{2b}$ |
| 3E6 | + | + | − | − | IgG$_1$ |

[a]Isotype specificity was determined using IsoStrip tests (Boehringer-Mannheim) for murine antibody isotype determinations which were conducted according to manufacturer's instructions.

Western blot analysis was conducted utilizing PSMA from a variety of sources, i.e., LNCaP cells, recombinant baculovirus expressed PSMA, and seminal fluid. The results generally indicate strong antibody binding to PSMA from all sources, and negative reactivity to lysates of PSMA negative PC-3 cells. In certain instances (antibodies 3E11, 2E4, 3G6, and 3F6), no reactivity to baculovirus expressed PMSA was observed although strong reactivity to LNCaP and seminal fluid derived PSMA was observed. Presumably, this was due to differences in crypticity of antibody epitopes in this region, perhaps as a result of the presence of the poly-histidine N-terminal substitution on the baculovirus expressed protein.

The thirty-two monoclonal antibodies can be grouped based upon their ability to bind to a faster migrating approximately 100 kDa protein band present in LNCaP cell lysates. Western blots were also conducted utilizing an LNCaP cell lysate depleted of full length PSMA by binding to 7E11.C5-Immunobeads. The results confirm binding to PSM' for all antibodies specific for PSMA fragments 134-437 and 438-750 of SEQ ID NO:2. In addition, antibodies 3C2 and 3C4 which are most reactive with the amino acid 1-173 fragments of SEQ ID NO:2; also bind to PSM'. This further indicates that the protein epitope for these antibodies is within PSM' and likely within the overlapping region between fragments 1-173 and 134-437 of SEQ ID NO:2.

These results suggest that antibodies 2E4 and 3E11 are specific for epitopes contained within the first 57 amino acids since neither binds to the protein band corresponding to PSM'. However, no reactivity with these two antibodies was observed to a peptide corresponding to the intracellular portion of full length PSMA. Furthermore, these antibodies are capable of binding to unfixed cells by FACS analysis, indicating they cannot be specific for epitopes contained within the transmembrane domain of the protein. Thus, antibodies 2E4 and 3E11 must bind to epitopes contained within the extracellular domain of PSMA, most likely between residues 44 and 57 of SEQ ID NO:2. This same analysis indicates that antibodies 3E6 and 4D8 (which bind to the 1-173 PSMA fragment but not the 134-437 fragment of SEQ ID NO:2) are specific for a portion of the PSMA protein between approximately residues 57-134 of SEQ ID NO:2 since both antibodies bind to the PSM' protein by Western blot.

FACS analysis using this panel of antibodies shows positive staining of PSMA expressing LNCaP cells. Strongest shifts were observed with antibodies 3C6, 1G3, 3C9, 3C4, 3G6, 3F6, 3E11, 1D11, 3D8, 1G9 and 4D4. Presumably, at least some of the variability in the extent of cellular staining with these antibodies is due to effects of glycosylation through the 10 potential N-linked sites which are distributed in the more C-terminal portion of the protein.

Immunocytochemistry was conducted on both live and fixed LNCaP cells using this panel of antibodies. In general, staining intensity of live cells mirrored results obtained by flow cytometry. Staining of fixed cells also was similar with some exceptions as discussed below.

Anti-PSMA antibody 7E11.C5 is specific for the first 6 amino acids of PSMA and is located on the intracellular side of the plasma membrane. Immunocytochemical staining of live LNCaP cells with 7E11.C5 was negative, whereas staining was strong in fixed cells. Thus, this result demonstrates the integrity of the live LNCaP cells used in immunocytochemistry relating to the inability of antibodies to cross the plasma membrane of live cells. Strong staining of live LNCaP cells by antibodies 3C6, 4D4, and 1G9 was observed, indicating that they bind to extracellularly distributed epitopes. Weak or negative staining of fixed cells was observed with these antibodies, confirming that these antibodies recognize native protein conformations which are destroyed by denaturation or fixation of the protein. These three antibodies may be particularly useful for in vivo diagnosis and therapy of tumors, including tumor imaging.

A sandwich ELISA was developed utilizing the IgM 4E10-1.14 antibody as a capture reagent followed by each IgG for detection. A sensitive linear response to antigen concentration was observed regardless of the antibody used for detection.

In conclusion, a total of thirty-two IgG monoclonal antibodies were selected with specificity for PSMA. The antibodies bind epitopes distributed throughout the extracellular domain of PSMA. FIG. 20 summarizes the distribution of antibody epitope specificities of these antibodies. Three antibodies are specific for more complex epitopes related to the native protein conformations. All IgG antibodies specific for the portion of PSMA (SEQ ID NO:2) encompassing residues 134-750 also bind PSM'.

9. Deposit of Cell Lines

The following hybridoma cell lines were deposited on Mar. 12, 1996, on Mar. 11, 1997 and on Mar. 17, 1998 with the American Type Culture Collection, P.O. Box 1549 Manassas, Va. 20108 USA, and assigned the following accession numbers:

| ATCC Accession No. | Hybridoma | Date |
|---|---|---|
| HB12060 | 3F5.4G6 | Mar. 12, 1996 |
| HB12309 | 3D7.1.1 | Mar. 11, 1997 |
| HB12310 | 4E10-1.14 | Mar. 11, 1997 |
| HB12489 | 1G3 | Mar. 17, 1998 |
| HB12495 | 1G9 | Mar. 17, 1998 |
| HB12490 | 2C7 | Mar. 17, 1998 |
| HB12494 | 3C4 | Mar. 17, 1998 |
| HB12491 | 3C6 | Mar. 17, 1998 |
| HB12484 | 3C9 | Mar. 17, 1998 |
| HB12486 | 3E6 | Mar. 17, 1998 |
| HB12488 | 3E11 | Mar. 17, 1998 |
| HB12485 | 3G6 | Mar. 17, 1998 |
| HB12493 | 4D4 | Mar. 17, 1998 |
| HB12487 | 4D8 | Mar. 17, 1998 |
| HB12492 | 4C8B9 | Mar. 17, 1998 |
| HB12664 | 3F6 | Mar. 16, 1999 |
| HB12678 | 2E4 | Mar. 16, 1999 |
| HB12665 | 3C2 | Mar. 16, 1999 |
| HB12672 | 2D4 | Mar. 16, 1999 |
| HB12660 | 4C8G8 | Mar. 16, 1999 |
| HB12675 | 2C4 | Mar. 16, 1999 |
| HB12663 | 4C11 | Mar. 16, 1999 |
| HB12661 | 1D11 | Mar. 16, 1999 |
| HB12667 | 4E8 | Mar. 16, 1999 |
| HB12674 | 2G5 | Mar. 16, 1999 |
| HB12620 | 4E6 | Mar. 16, 1999 |
| HB12677 | 1F4 | Mar. 16, 1999 |
| HB12666 | 2E3 | Mar. 16, 1999 |
| HB12662 | 3D8 | Mar. 16, 1999 |
| HB12668 | 4F8 | Mar. 16, 1999 |
| HB12673 | 3D2 | Mar. 16, 1999 |
| HB12676 | 1G7 | Mar. 16, 1999 |
| HB12669 | 3D4 | Mar. 16, 1999 |
| HB12679 | 5G10 | Mar. 16, 1999 |
| HB12671 | 5E9 | Mar. 16, 1999 |

The present invention is not to be limited in scope by the exemplified embodiments which are intended as illustrations of single aspects of the invention. Indeed, various modifications of the invention in addition to those shown and described herein will become apparent to those skilled in the art from the foregoing description and accompanying drawings. Such modifications are intended to fall within the scope of the appended claims.

All publications cited herein are incorporated by reference in their entirety.

What is claimed is:

1. A method of detecting the presence of PSMA expressed by prostate cancer cells, comprising contacting a sample of cells in vivo with a first monoclonal antibody having an antigen-binding region which binds to a native conformation of PSMA on the surface of live cells and not to denatured PSMA and not to PSMA on the surface of fixed cells and detecting any antibody-bound PSMA on the membrane of the prostate cancer cells.

2. The method of claim 1, in which the antigen-binding region of the antibody competitively inhibits the immunospecific binding of a second monoclonal antibody to its target epitope, said second antibody being produced by a hybridoma selected from 3C6 having ATCC accession number HB 12491, 4D4 having ATCC accession number HB 12493, and 1G9 having ATCC accession number HB 12495.

3. The method of claim 2, wherein the second monoclonal antibody is produced by hybridoma 3C6 having ATCC accession number HB 12491.

4. The method of claim 2, wherein the second monoclonal antibody is produced by hybridoma 4D4 having ATCC accession number HB 12493.

5. The method of claim 2, wherein the second monoclonal antibody is produced by hybridoma 1G9 having ATCC accession number HB 12495.

6. The method of claim 1, wherein the antibody is produced by a hybridoma selected from 3C6 having ATCC accession number HB 12491, 4D4 having ATCC accession number HB 12493, and 1G9 having ATCC accession number HB 12495.

7. The method of claim 1 in which the prostate cancer cells are metastatic prostate cancer cells.

8. The method of claim 1 in which the antibody is conjugated to a radioisotope.

9. A method of targeting PSMA expressed by prostate cancer cells in a subject, the method comprising administering to the subject a monoclonal antibody having an antigen-binding region which binds to PSMA expressed on the membrane of live cells and not to denatured PSMA and not to PSMA on the surface of fixed cells whereby the monoclonal antibody targets PSMA on the membrane of the prostate cancer cells in the subject.

10. The method of claim 9, wherein the antigen-binding region of the antibody competitively inhibits the immunospecific binding of a second monoclonal antibody to its target epitope, said second antibody is produced by a hybridoma selected from 3C6 having ATCC accession number HB 12491, 4D4 having ATCC accession number HB 12493, and 1G9 having ATCC accession number HB 12495.

11. The method of claim 10, wherein the antibody is produced by a hybridoma selected from 3C6 having ATCC accession number HB 12491, 4D4 having ATCC accession number HB 12493, and 1G9 having ATCC accession number HB 12495.

12. The method of claim 10, wherein the antibody is conjugated to a radioisotope.

13. A method of targeting PSMA expressed by prostate cancer cells in a subject, the method comprising administering to the subject a first monoclonal antibody having an antigen-binding region which binds to a native conformation of PSMA on the surface of live cells and not to denatured PSMA and not to PSMA on the surface of fixed cells whereby the monoclonal antibody targets PSMA on the membrane of the prostate cancer cells in the subject.

14. The method of claim 13, wherein the antigen-binding region of the antibody competitively inhibits the immunospecific binding of a second monoclonal antibody to its target epitope, said second antibody is produced by a hybridoma selected from 3C6 having ATCC accession number HB 12491, 4D4 having ATCC accession number HB 12493, and 1G9 having ATCC accession number HB 12495.

15. The method of claim 13, wherein the antibody is produced by a hybridoma selected from 3C6 having ATCC accession number HB 12491, 4D4 having ATCC accession number HB 12493, and 1G9 having ATCC accession number HB 12495.

16. The method of claim 13, wherein the antibody is conjugated to a radioisotope.

* * * * *

SEQUENCE LISTING

```
<160> NUMBER OF SEQ ID NOS: 2

<210> SEQ ID NO 1
<211> LENGTH: 8
<212> TYPE: PRT
<213> ORGANISM: Homo sapiens

<400> SEQUENCE: 1

Glu Ser Lys Val Asp Pro Ser Lys
 1               5

<210> SEQ ID NO 2
<211> LENGTH: 750
<212> TYPE: PRT
<213> ORGANISM: Homo sapiens

<400> SEQUENCE: 2

Met Trp Asn Leu Leu His Glu Thr Asp Ser Ala Val Ala Thr Ala Arg
 1               5                  10                  15

Arg Pro Arg Trp Leu Cys Ala Gly Ala Leu Val Leu Ala Gly Gly Phe
                20                  25                  30

Phe Leu Leu Gly Phe Leu Phe Gly Trp Phe Ile Lys Ser Ser Asn Glu
            35                  40                  45

Ala Thr Asn Ile Thr Pro Lys His Asn Met Lys Ala Phe Leu Asp Glu
        50                  55                  60

Leu Lys Ala Glu Asn Ile Lys Lys Phe Leu Tyr Asn Phe Thr Gln Ile
    65                  70                  75                  80

Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Ala His
                100                 105                 110

Tyr Asp Val Leu Leu Ser Tyr Pro Asn Lys Thr His Pro Asn Tyr Ile
            115                 120                 125
```

-continued

```
Ser Ile Ile Asn Glu Asp Gly Asn Glu Ile Phe Asn Thr Ser Leu Phe
            130                 135                 140

Glu Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
            180                 185                 190

Lys Ile Asn Cys Ser Gly Lys Ile Val Ile Ala Arg Tyr Gly Lys Val
            195                 200                 205

Phe Arg Gly Asn Lys Val Lys Asn Ala Gln Leu Ala Gly Ala Lys Gly
210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Val Gln Arg Gly
                245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg Arg Gly Ile Ala Glu Ala Val Gly
            275                 280                 285

Leu Pro Ser Ile Pro Val His Pro Ile Gly Tyr Tyr Asp Ala Gln Lys
290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Asn Glu Val
            340                 345                 350

Thr Arg Ile Tyr Asn Val Ile Gly Thr Leu Arg Gly Ala Val Glu Pro
            355                 360                 365

Asp Arg Tyr Val Ile Leu Gly His Arg Asp Ser Trp Val Phe Gly
370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
                405                 410                 415

Leu Phe Ala Ser Trp Asp Ala Trp Trp Phe Gly Leu Leu Gly Ser Thr
            420                 425                 430

Glu Trp Ala Glu Glu Asn Ser Arg Leu Leu Gln Glu Arg Gly Val Ala
            435                 440                 445

Tyr Ile Asn Ala Asp Ser Ser Ile Glu Gly Asn Tyr Thr Leu Arg Val
450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Glu Ser
                485                 490                 495

Trp Thr Lys Lys Ser Pro Ser Pro Glu Phe Ser Gly Met Pro Arg Ile
            500                 505                 510

Ser Lys Leu Gly Ser Gly Asn Asp Phe Glu Val Phe Phe Gln Arg Leu
            515                 520                 525

Gly Ile Ala Ser Gly Arg Ala Arg Tyr Thr Lys Asn Trp Glu Thr Asn
530                 535                 540

Lys Phe Ser Gly Tyr Pro Leu Tyr His Ser Val Tyr Glu Thr Tyr Glu
```

```
-continued 545                    550                    555                    560
Leu Val Glu Lys Phe Tyr Asp Pro Met Phe Lys Tyr His Leu Thr Val
                565                    570                    575

Ala Gln Val Arg Gly Gly Met Val Phe Glu Leu Ala Asn Ser Ile Val
                580                    585                    590

Leu Pro Phe Asp Cys Arg Asp Tyr Ala Val Val Leu Arg Lys Tyr Ala
            595                    600                    605

Asp Lys Ile Tyr Ser Ile Ser Met Lys His Pro Gln Glu Met Lys Thr
        610                    615                    620

Tyr Ser Val Ser Phe Asp Ser Leu Phe Ser Ala Val Lys Asn Phe Thr
625                    630                    635                    640

Glu Ile Ala Ser Lys Phe Ser Glu Arg Leu Gln Asp Phe Asp Lys Ser
                645                    650                    655

Asn Pro Ile Val Leu Arg Met Met Asn Asp Gln Leu Met Phe Leu Glu
                660                    665                    670

Arg Ala Phe Ile Asp Pro Leu Gly Leu Pro Asp Arg Pro Phe Tyr Arg
            675                    680                    685

His Val Ile Tyr Ala Pro Ser Ser His Asn Lys Tyr Ala Gly Glu Ser
        690                    695                    700

Phe Pro Gly Ile Tyr Asp Ala Leu Phe Asp Ile Glu Ser Lys Val Asp
705                    710                    715                    720

Pro Ser Lys Ala Trp Gly Glu Val Lys Arg Gln Ile Tyr Val Ala Ala
                725                    730                    735

Phe Thr Val Gln Ala Ala Ala Glu Thr Leu Ser Glu Val Ala
                740                    745                    750
```